US012226635B2

(12) United States Patent
Soin

(10) Patent No.: US 12,226,635 B2
(45) Date of Patent: Feb. 18, 2025

(54) METHOD AND SYSTEM FOR AUTOMATED NEUROMODULATION THROUGH MACHINE LEARNING

(71) Applicant: Soin Neuroscience, LLC, Dayton, OH (US)

(72) Inventor: Amol N. Soin, Dayton, OH (US)

(73) Assignee: Soin Neuroscience, LLC, Dayton, OH (US)

( * ) Notice: Subject to any disclaimer, the term of this patent is extended or adjusted under 35 U.S.C. 154(b) by 608 days.

(21) Appl. No.: 17/408,890

(22) Filed: Aug. 23, 2021

(65) Prior Publication Data

US 2021/0379381 A1    Dec. 9, 2021

Related U.S. Application Data

(63) Continuation of application No. 16/787,877, filed on Feb. 11, 2020, now abandoned.

(51) Int. Cl.
*A61N 1/05*    (2006.01)
*A61N 1/36*    (2006.01)

(52) U.S. Cl.
CPC ....... *A61N 1/36071* (2013.01); *A61N 1/0551* (2013.01); *A61N 1/36132* (2013.01);
(Continued)

(58) Field of Classification Search
CPC ............ A61N 1/36139; A61N 1/36132; A61N 1/37282; A61N 1/37288; A61N 1/3607
See application file for complete search history.

(56) References Cited

U.S. PATENT DOCUMENTS

| 5,800,535 A | 9/1998 | Howard, III |
| 6,270,457 B1 * | 8/2001 | Bardy ................... A61B 5/686 |
| | | 128/920 |

(Continued)

FOREIGN PATENT DOCUMENTS

| WO | 2017127902 A1 | 8/2017 |
| WO | 2018093765 A1 | 5/2018 |

OTHER PUBLICATIONS

International Search Report and Written Opinion for PCT/US20/19587; Jul. 20, 2020.
(Continued)

*Primary Examiner* — Alyssa M Alter
(74) *Attorney, Agent, or Firm* — Neustel Law Offices

(57) ABSTRACT

An automated neuromodulation system which uses patient feedback during a training phase in combination with machine learning to automatically provide optimal nerve stimulation parameters based on the patient's needs without patient input. The automated neuromodulation system generally includes a lead which is implanted in a patient for treatment of a wide range of conditions, such as chronic pain. The patient is provided with a remote control through which the patient may provide either positive or negative feedback relating to how the patient is responding to electrical stimulation in different situations. A control unit monitors feedback from the patient as well as information and data from the time of feedback, such as the patient's position, orientation, speed of movement, or other considerations. Using machine learning, the control unit may process the feedback and data to formulate an optimized neuromodulation protocol and criteria which may be automatically applied to the patient.

10 Claims, 22 Drawing Sheets

(52) U.S. Cl.
CPC ...... *A61N 1/36139* (2013.01); *A61N 1/36007* (2013.01); *A61N 1/36064* (2013.01); *A61N 1/36067* (2013.01); *A61N 1/36082* (2013.01)

(56) References Cited

U.S. PATENT DOCUMENTS

| | | | |
|---|---|---|---|
| 8,401,666 | B2 | 3/2013 | Skelton |
| 9,782,122 | B1 | 10/2017 | Pulliam |
| 9,789,313 | B2 | 10/2017 | Lipani |
| 9,931,508 | B2 | 4/2018 | Burdick |
| 10,183,167 | B2 | 1/2019 | Steinke |
| 10,449,371 | B2 | 10/2019 | Serrano Carmona |
| 2006/0235472 | A1* | 10/2006 | Goetz ............... A61N 1/37264 604/890.1 |
| 2009/0083070 | A1 | 3/2009 | Giftakis |
| 2013/0096641 | A1 | 4/2013 | Strother |
| 2016/0082265 | A1 | 3/2016 | Moffitt |
| 2017/0056642 | A1 | 3/2017 | Moffitt |
| 2017/0080234 | A1 | 3/2017 | Gillespie |
| 2017/0157410 | A1 | 6/2017 | Moffitt |
| 2017/0319856 | A1 | 11/2017 | Moffitt |
| 2019/0184168 | A1 | 6/2019 | Vansickle |
| 2019/0365228 | A1 | 12/2019 | Rondoni |

OTHER PUBLICATIONS https://www.fda.gov/medical-devices/recently-approved-devices/boston-scientific-spinal-cord-stimulation-system-p030017s275; Boston Scientific Spinal Cord Stimulation; Dec. 8, 2017.
European Extended Search Report and Opinion for European Application No. 20918282.3; Jan. 31, 2024.

* cited by examiner

METHOD AND SYSTEM FOR AUTOMATED NEUROMODULATION THROUGH MACHINE LEARNING

CROSS REFERENCE TO RELATED APPLICATIONS

The present application is a continuation of U.S. application Ser. No. 16/787,877 filed on Feb. 11, 2020. Each of the aforementioned patent applications is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to a method and system for automated neuromodulation through machine learning which uses patient feedback during a training phase in combination with machine learning to automatically provide optimal nerve stimulation parameters based on the patient's needs without patient input.

Related Art

Any discussion of the related art throughout the specification should in no way be considered as an admission that such related art is widely known or forms part of common general knowledge in the field.

Neuromodulation by electrical stimulation is known the medical arts for treatment of a wide range of conditions such as, for example, management of intractable pain. Neuromodulation may be used for a wide range of symptoms, such as but not limited to chronic critical limb ischaemia, angina pectoris and in other visceral pain syndromes including chronic pancreatitis, chronic painful bladder syndrome and chronic abdominal pain. For example, spinal cord stimulation (SCS) has been used for over 50 years for therapeutic treatment of pain. Deep brain stimulation was also developed in the past 40 years which may be used for treatment of movement disorder symptoms, such as symptoms of Parkinson's disease, dystonia, or essential tremor.

Neuromodulation treats pain, particularly nerve pain, through the alteration of nerve activity through the targeted delivery of a stimulus, such as electrical stimulation. A common device used for neuromodulation is an implantable pulse generator which is implanted into the patient. Leads having electrodes are connected to the implantable pulse generator and implanted near a nerve or bundle of nerves to be stimulated. Electrical stimulation of nerves may stimulate nerve cell activity by releasing transmitters, such as dopamine, that can modulate the excitability and firing patterns of neural circuits.

In the past, pulse generators have largely been manually operated by either a patient or a health care provider. The patient may provide real-time feedback, such as through a remote control, to increase or decrease levels of electrical stimulation. However, such systems are dependent on continuous real-time feedback from the patient to continuously maintain adequate stimulation levels for treatment of pain. It would be much more effective if a system were able to automatically determine criteria and protocols for a particular patient, such as through machine learning, to automate the neuromodulation of the patient for treatment of a wide range of conditions.

SUMMARY

An example embodiment is directed to a method and system for automated neuromodulation through machine learning. The method and system for automated neuromodulation through machine learning includes a lead which is implanted in a patient for treatment of a wide range of conditions, such as chronic pain, movement disorders, incontinence, constipation, or other neurological disorders. A pulse generator is in communication with the lead such that the lead may emit electrical stimulation. The patient is provided with a remote control through which the patient may provide either positive or negative feedback relating to how the patient is responding to electrical stimulation in different situations. A training phase may be conducted during which the patient is prompted to perform various tasks or activities while different levels of electrical stimulation are applied. A control unit monitors feedback from the patient as well as information and data from the time of feedback, such as the patient's position, orientation, speed of movement, or other considerations which may be detected by a sensor. Using machine learning, the control unit may process the information and data from the patient to formulate an optimized neuromodulation protocol and criteria which may be automatically applied to the patient by the pulse generator. Overtime, data stored in a data base may use machine learning to develop typical algorithms for similar patients and allow for artificial intelligent derived stimulation patterns obtained from machine learning for automated stimulation programs.

There has thus been outlined, rather broadly, some of the embodiments of the method and system for automated neuromodulation through machine learning in order that the detailed description thereof may be better understood, and in order that the present contribution to the art may be better appreciated. There are additional embodiments of the method and system for automated neuromodulation through machine learning that will be described hereinafter and that will form the subject matter of the claims appended hereto. In this respect, before explaining at least one embodiment of the method and system for automated neuromodulation through machine learning in detail, it is to be understood that the method and system for automated neuromodulation through machine learning is not limited in its application to the details of construction or to the arrangements of the components set forth in the following description or illustrated in the drawings. The method and system for automated neuromodulation through machine learning is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

DETAILED DESCRIPTION

Figure 1:
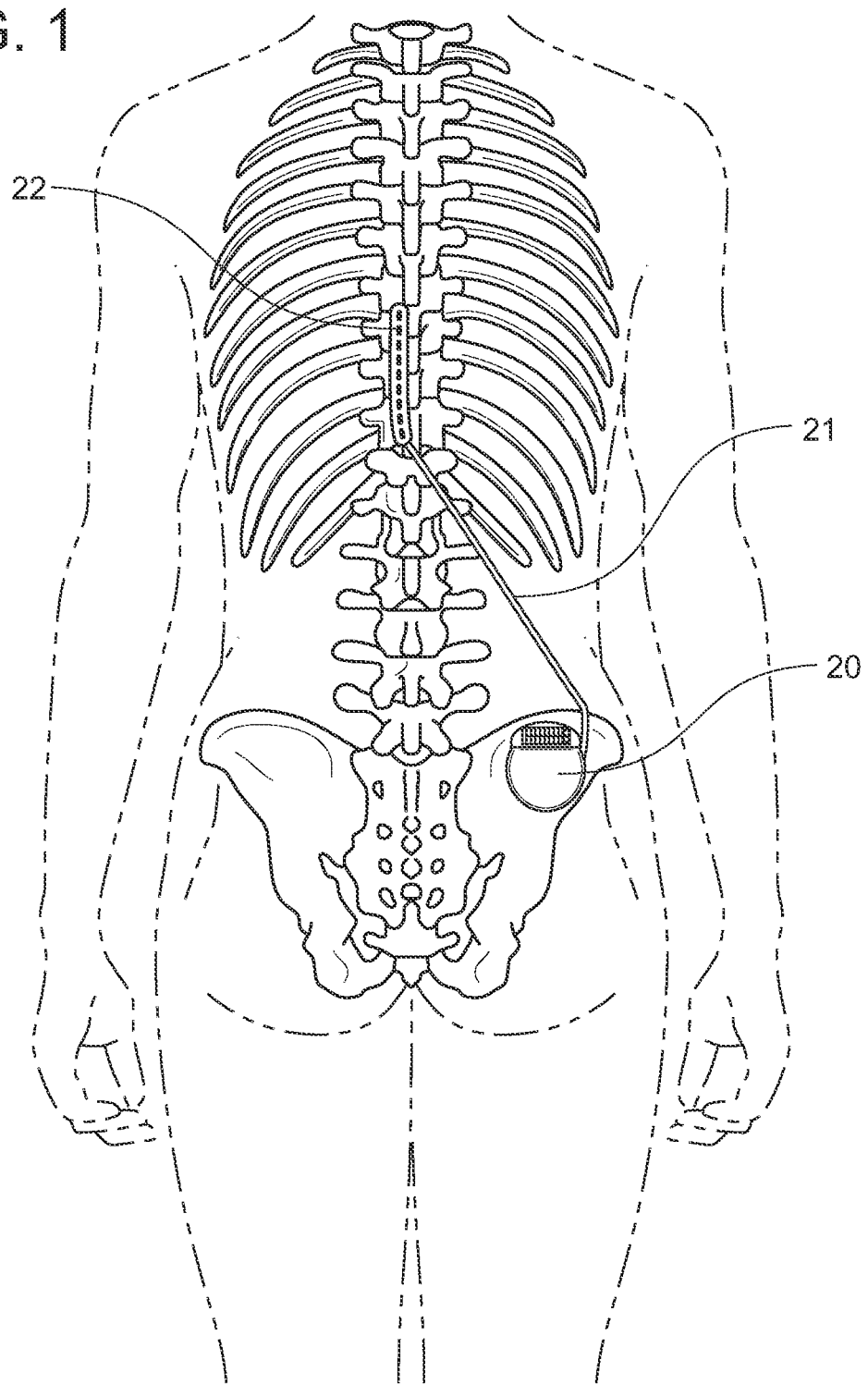
FIG. 1 is an internal view of an implanted pulse generator of a method and system for automated neuromodulation through machine learning in accordance with an example embodiment.

A. Overview.

An example method and system for automated neuromodulation through machine learning 10 generally comprises a pulse generator 20 which is used for treatment of an ailment in a patient 12, wherein the pulse generator 20 is adapted to periodically emit an electrical stimulation. In some embodiments, the pulse generator 20 may be implanted in the patient 12. In other embodiments, an external pulse generator 20 may be utilized. In such embodiments, the pulse generator 20 may be external and in wireless communication with a lead 22.

A lead 22 is in communication with the pulse generator 20, the lead 22 being connected to or near an afflicted area of the patient 12 so as to apply the electrical stimulation from the pulse generator 20 to the afflicted area of the patient 12. In some embodiments, the lead 22 may be implanted. A sensor 24 may be adapted to detect a condition of the patient 12. A control unit 30 is communicatively connected to the pulse generator 20, wherein the control unit 30 is communicatively connected to the sensor 24.

A remote control 40 may be communicatively connected to the control unit 39, wherein the remote control 40 comprises a first input 41 and a second input 42 for the patient 12 to provide patient feedback to the electrical stimulation, wherein the first input 41 is adapted to be selected by the patient to indicate a positive feedback to the electrical stimulation by the pulse generator 20, wherein the second input 42 is adapted to be selected by the patient 12 to indicate a negative feedback to the electrical stimulation by the pulse generator 20.

The control unit 30 is adapted to process the patient feedback previously received from the patient 12 and the condition of the patient 12 at the time of the patient feedback to formulate an electrical stimulation protocol for the patient 12, wherein the pulse generator 20 is adapted to automatically apply the electrical stimulation protocol to the patient 12 depending on the condition of the patient 12 based on the positive feedback or the negative feedback previously received from the patient 12.

The sensor 24 may be implanted in the patient 12 or external to the patient 12. The sensor 24 may be connected to the pulse generator 20 or may be connected to the lead 22. The sensor 24 may be comprised of an accelerometer and/or a gyroscope. The condition detected by the sensor 24 may comprise a position and orientation of the patient. The condition detected by the sensor 24 may also comprise a movement speed of the patient. The ailment being treated may be comprised of nerve pain and the afflicted area of the patient may be comprised of a nerve. In other embodiments, the ailment being treated may comprise movement disorders, seizure disorders, bowel and bladder dysfunction, obesity, chronic pain, ischemia, psychiatric conditions, and the like. It should be appreciated that a wide range of ailments may be treated by the systems and methods described herein, and thus the scope should not be construed as limited to any particular ailment. The lead 22 may be connected to a spinal cord of the patient 12. The remote control 40 may be comprised of a key fob 45 or a smart phone 46. The sensor 24 may be comprised of a smart phone.

A method of developing an automated neuromodulation protocol with the method and system for automated neuromodulation through machine learning 10 may be comprised of the steps of implanting the lead 22 in the patient 12, connected the lead 22 to the afflicted area of the patient 12, establishing communication between the lead 22 and the pulse generator 20, conducting a training phase with the patient 12 during which different levels of electrical stimulation are applied to the patient 12 by the pulse generator 20 via the lead 22 while the patient performs an activity, receiving feedback data from the patient 12 via the remote control 40 during the training phase by the control unit 30, processing feedback data from the patient 12 to formulate an automated neuromodulation protocol, wherein the automated neuromodulation protocol comprises a plurality of levels of the electrical stimulation to be applied depending on the activity of the patient 12, and automatically applying the electrical stimulation to the patient 12 by the lead 22 via the pulse generator 20 based on the automated neuromodulation protocol. The activity may be comprised of walking around a room by the patient or may be comprised of standing up from a sitting position by the patient.

Another exemplary embodiment of a method and system for automated neuromodulation through machine learning 10 may be comprised of a plurality of pulse generators 20, each of the plurality of pulse generators 20 being implanted or used externally within one of a plurality of patients 12 to periodically emit an electrical stimulation, wherein each of the plurality of pulse generators 20 is in communication with a lead 22 adapted to be connected to an afflicted area of one of the plurality of patients 12; a plurality of control units 30, each of the control units 30 being communicatively connected to one of the plurality of pulse generators 20; a plurality of sensors 24, each of the sensors 24 being communicatively connected to one of the plurality of control units 30, wherein each of the plurality of sensors 24 is adapted to detect a condition of one of the plurality of patients 12; a plurality of remote controls 40, each of the remote controls 40 being communicatively connected to one of the plurality of control units 30 and one of the plurality of pulse generators 20, wherein each of the plurality of remote controls 40 comprises an input 41, 42 for providing patient feedback to the electrical stimulation; a remote server 50 including a central database 52, wherein each of the plurality of control units 30 is communicatively connected to the remote server 50; wherein the control unit 30 is adapted to transmit the patient feedback and the condition of one of the plurality of patients 12 at a time of the patient feedback to the remote server 50; wherein the remote server 50 is adapted to process the patient feedback and the condition of one of the plurality of patients 12 at a time of the patient feedback to formulate a baseline electrical stimulation protocol to be applied to a new patient, wherein the baseline electrical stimulation protocol comprises criteria for application of the electrical stimulation based on the condition of the new patient. The baseline electrical stimulation protocol may be continuously updated by the remote server 50 and may be stored on the central database 52.

B. Pulse Generator.

Figure 2:
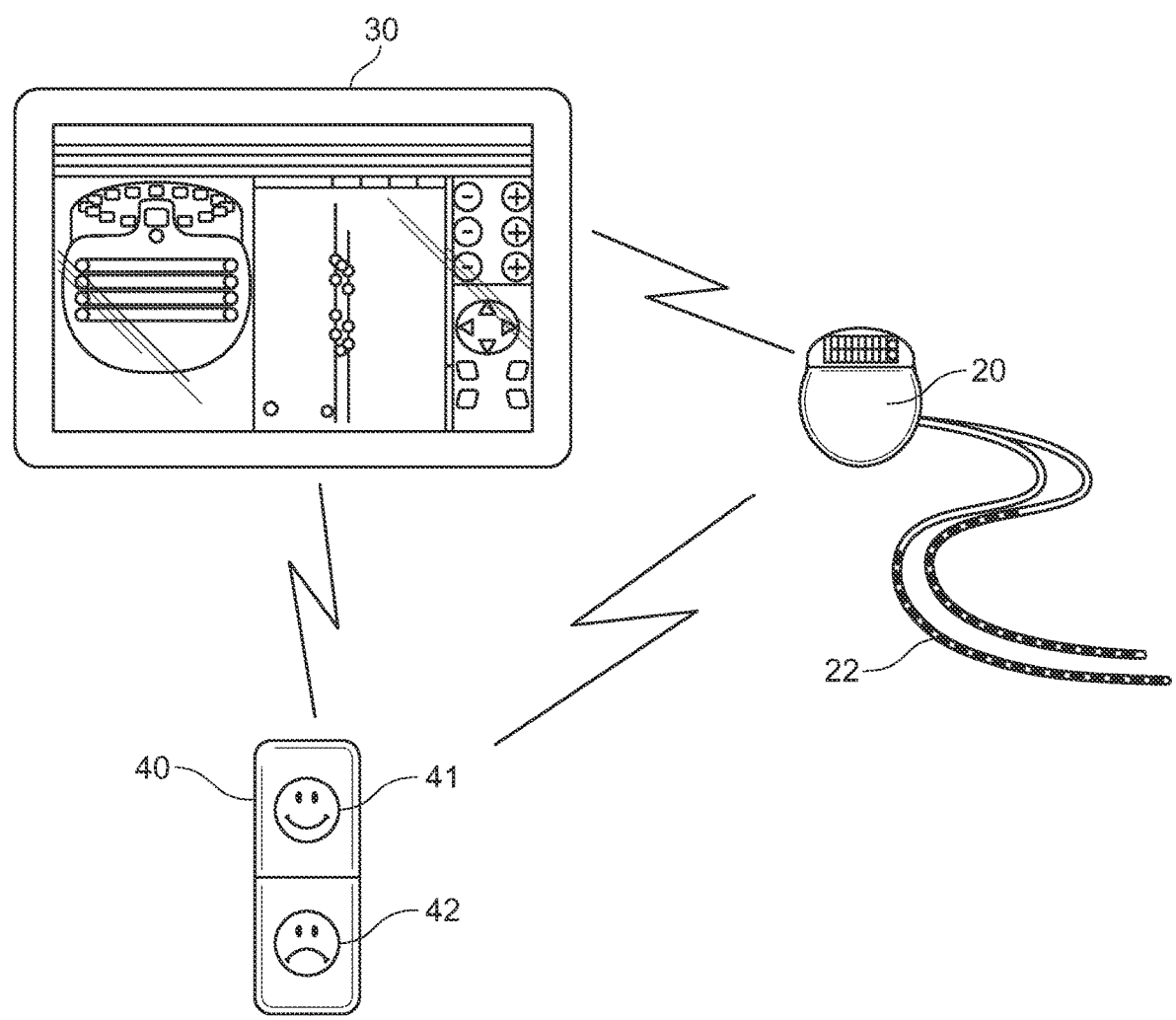
FIG. 2 is a frontal view of a method and system for automated neuromodulation through machine learning in accordance with an example embodiment.
Figure 3:
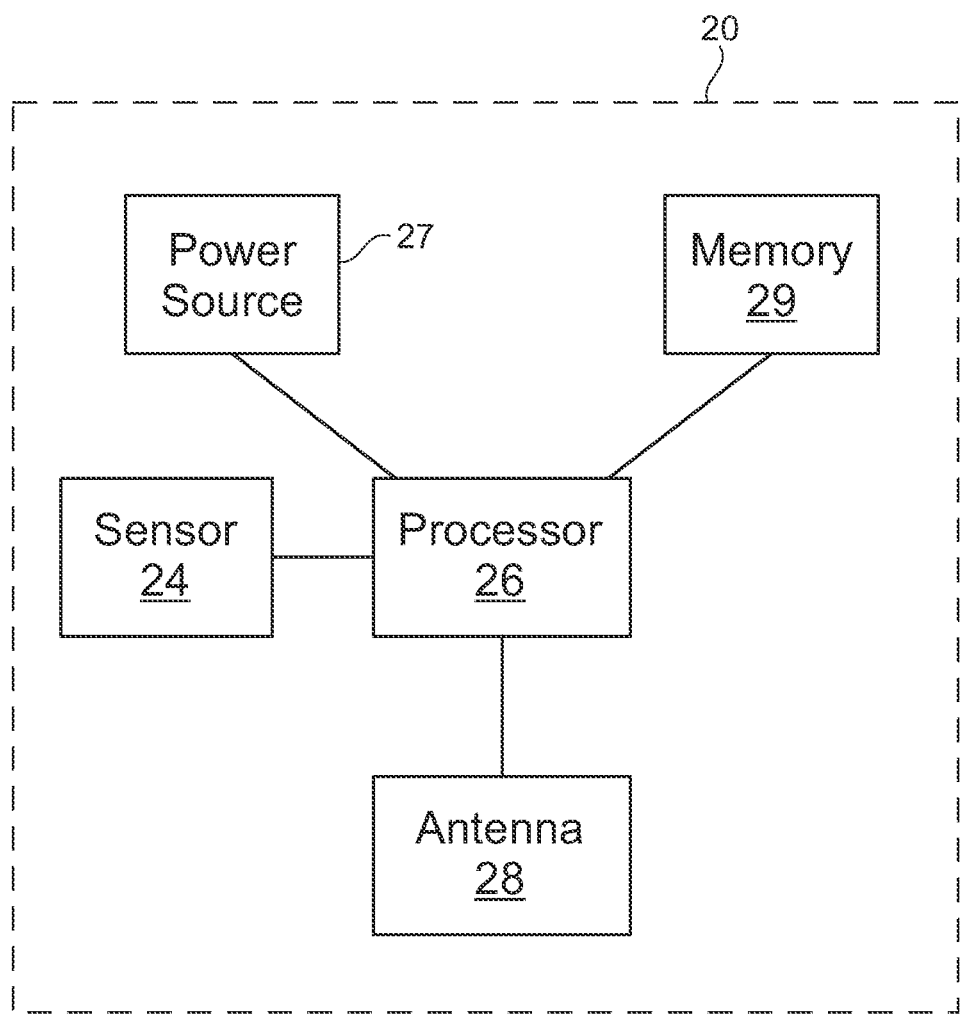
FIG. 3 is a block diagram of an exemplary pulse generator of a method and system for automated neuromodulation through machine learning in accordance with an example embodiment.

FIGS. 1-3 illustrate an exemplary pulse generator 20 for use with the systems and methods described herein. A pulse generator 20 is generally known in the art for use as a neurostimulator. Such neurostimulators are typically used for treatment of chronic pain such as intractable plain of the trunk and/or limbs. Other conditions which may be treated by neurostimulators and benefit from the systems and methods described herein may include spinal conditions requiring spinal stimulators, bladder conditions, incontinence, deep brain stimulators, vagus nerve stimulators, and the like.

An exemplary condition which is typically treated with a pulse generator 20 is complex regional pain syndrome (CRPS) Types I and II. It should be appreciated that the methods and systems described herein may be applied to any number of conditions which are treatable by electrical stimulation of one or more nerves.

The pulse generator 20 may be implanted within the body of the patient 12, such as via a small incision in the patient's back. The positioning and implantation method of the pulse generator 20 may vary in different embodiments and should not be construed as limiting in scope. An exemplary position of the pulse generator 20, in which the pulse generator 20 has been implanted in the lower back of a patient 12, is shown in FIG. 1. However, it should be appreciated that the positioning of both the pulse generator 20 and the leads 22 shown in FIG. 1 are merely for illustrative purposes, and thus are not intended to limit the scope of where and how the pulse generator 20 may be implanted in a patient 12.

In some embodiments, the pulse generator 20 may be external to the body, with the leads 22 being internal to the body. In such embodiments, the pulse generator 20 may be carried or worn by the patient 12, with only the leads 22 being implanted in the body. In some embodiments, the pulse generator 20 may be both external and wired to the leads 22. Such a configuration is less desirable than a full implantation, however, as the entry site of the extension wires 21 or leads 22 may be prone to infection and the mobility of the patient 12 may be reduced with such an external installation. In other embodiments, the pulse generator 20 may be external to the body and in communication, such as wireless communication, with the leads 22. In such embodiments, the pulse generator 20 may communicate with the leads 22 by various communications protocols, such as but not limited to radio frequency (RF) antenna signals. In such embodiments, the sensor 24 may be also be external to the body and may be incorporated with the pulse generator 20.

In response to directions from the patient 12 or staff, the pulse generator 20 will apply electrical stimulation to one or more nerves via the leads 22 in an effort to reduce or eliminate pain in the patient 12. The pulse generator 20 is generally used on patients 12 for whom traditional pain management through medications has been shown to be ineffective. As discussed in more detail below, after installation of the pulse generator 20, a training phase will be undertaken to "train" the pulse generator 20 to function optimally for that particular patient 12.

FIGS. 1 and 3 illustrate an exemplary embodiment of a pulse generator 20. As shown in the figures, the pulse generator 20 is generally comprised of a small, box-shaped device which is adapted to be implanted within the body of the patient 12. In some embodiments, the pulse generator 20 may instead be not implanted within the body of the patient 12, but instead worn or carried externally by the patient 12.

The pulse generator 20 may include internal circuitry including an internal power source 27 such as a battery. In modern pulse generators 20, a lithium-iodine battery is generally used, though other types of power sources 27 may be utilized. The internal circuitry of a typical pulse generator 20 will generally include sensing, output, telemetry, and diagnostic circuits. An antenna 28 may be incorporated into the pulse generator 20 to transmit or receive data, such as with a control unit 30. In embodiments in which the leads 22 are implanted and the pulse generator 20 is external to the body of the patient 12, the antenna 28 of the pulse generator 20 may be utilized to establish communication between the pulse generator 20 and the leads 22. The pulse generator 20 may include an internal processor 26 and memory 29 in some embodiments such as shown in FIG. 3.

As can be seen in FIG. 1, the pulse generator 20 includes at least one lead 22 which is adapted to apply electrical stimulation to the relevant nerve(s) for treatment of pain. In embodiments in which the target site is a distance from the implanted pulse generator 20, an extension conduit 21 such as an insulated wire may be used to connect the pulse generator 20 to the lead 22 such as shown in FIG. 1. The lead 22 may include an electrode which is connected to a nerve of the patient 12. A typical pulse generator 20 may include two leads 22. The lead 22 may be connected to a neural tissue or, in some embodiments, may be connected to a non-neural tissue.

Figure 5A:
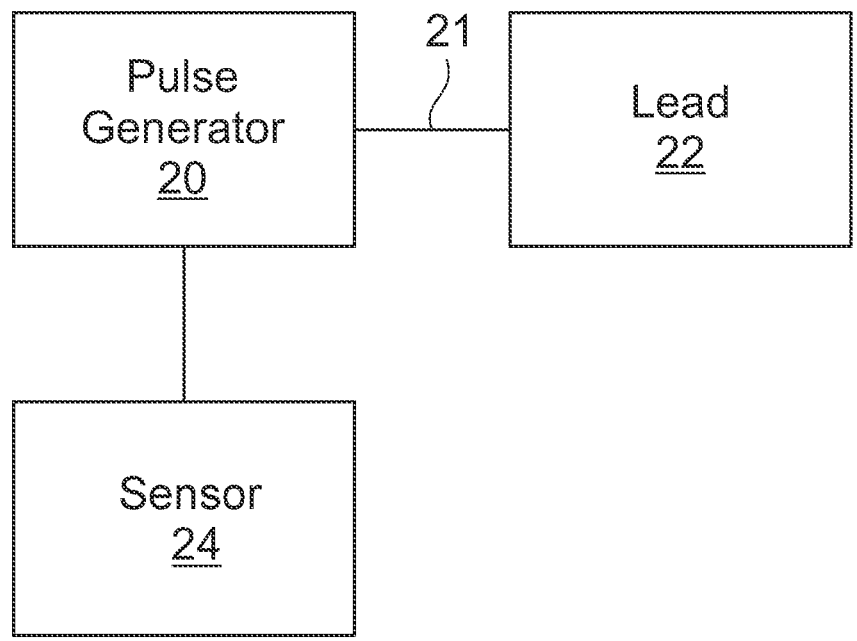
FIG. 5A is a block diagram of a sensor connected to a pulse generator of a method and system for automated neuromodulation through machine learning in accordance with an example embodiment.
Figure 5B:
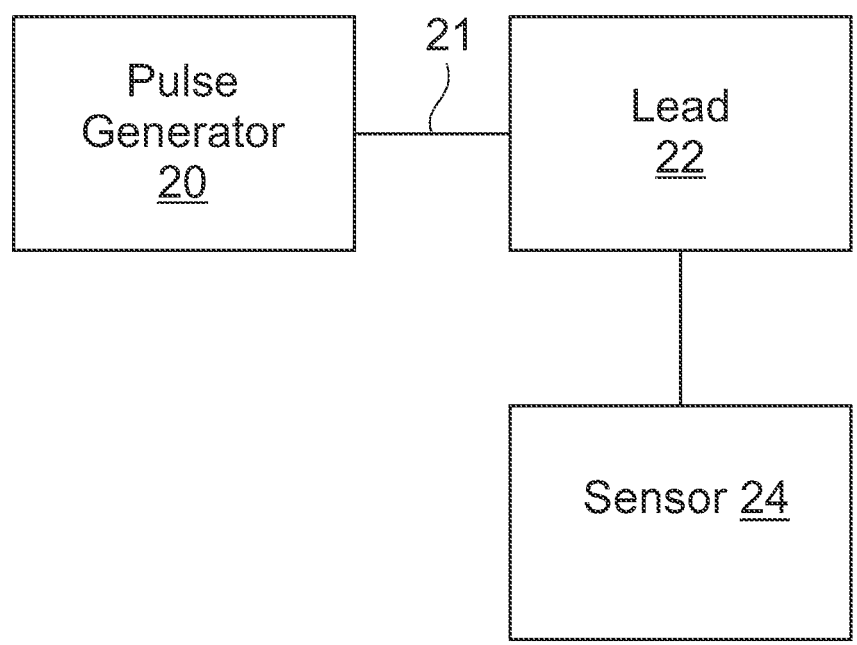
FIG. 5B is a block diagram of a sensor connected to a lead of a method and system for automated neuromodulation through machine learning in accordance with an example embodiment.

As shown in FIGS. 3, 5A, and 5B, the pulse generator 20 and/or leads 22 may include a sensor 24 for measuring and/or detecting various attributes and factors related to the position, orientation, and movement of the patient 12. The sensor 24 is utilized to determine the orientation and position of the patient 12, such as, for example, to determine if the patient 12 is sitting, standing, or lying down, at any given time. The sensor 24 may also be utilized to determine speed of movement of the patient 12 which can be utilized, for example, to determine if the patient 12 is dormant, walking, or running.

The sensor 24 may be comprised of various types of sensors known in the art, including but not limited to accelerometers and gyroscopes. The sensor 24 may be installed as part of the pulse generator 20, such as shown in FIGS. 3 and 5A, or may be connected to the leads 22, such as shown in FIG. 5B, or extension wire 21 in some embodiments. By way of example and without any limitation, the sensor 24 in some embodiments could comprise an MPU 6050 chip which includes a MEMS 3-axis gyroscope and a 3-axis accelerometer with an onboard digital motion processor. A further example of a sensor 24 may comprise an MPU9250 9-axis gyroscope/accelerometer chip.

The sensor 24 may be implantable, or may be external to the body of the patient 12. The sensor 24 may be implanted at various locations in the body of the patient 12. In some cases, the sensor 24 may be remotely located with respect to the pulse generator 20, extension wire 21, and leads 22, so long as the sensor 24 is communicatively interconnected with the pulse generator 20 and/or control unit 30. By way of example and without limitation, the sensor 24 may comprise the STMicroelectronics MIS2DH ultra-low power implantable motion sensor which includes a 3-axis accelerometer. In some embodiments, the pulse generator 20 may be communicatively interconnected with the remote control 40 in a manner which allows the remote control 40 to perform the functions of the sensor 24.

FIG. 2 illustrates exemplary components of an example embodiment of a method and system for automated neuromodulation through machine learning 10 which comprises a pulse generator 20 including leads 22 extending from the pulse generator 20, a control unit 30, and a remote control 40. Although shown outside of the patient's 12 body for clarity, it should be appreciated that the pulse generator 20 and leads 22 will generally be implanted in the patient 12. The pulse generator 20 is communicatively interconnected with both the remote control 40 and the control unit 30 such as shown in FIG. 3. Although not shown, the pulse generator 20 will generally include an internal antenna which allows for wireless communications with the control unit 30 and/or remote control 40.

C. Control Unit.

The control unit 30 will generally comprise a computer system such as a laptop, desktop computer, smart phone, tablet computer, or the like. The control unit 30 may include a processor 32 and memory 34. The processor 32 may be utilized to perform various data processing functions. The memory 34 may be used to store various data, such as feedback data from the patient 12 during the training phase or data received from the remote server 50 regarding optimal parameters as learned from other patients 12.

The control unit 30 may be utilized for processing data from the remote control 40 or other external devices when during the training phase. The control unit 30 will generally be configured to store and process data related to patient feedback received from the remote control 40 as discussed below. The control unit 30 may also be configured to receive commands and inputs from staff such as a nurse or doctor, or from the patient 12.

As discussed below, the control unit 30 may perform machine learning functionality based on feedback from the patient 12 and medical staff so as to automate stimulation parameters based on variable circumstances such as patient 12 positioning, orientation, and activity (such as walking, running, sitting, etc.). The control unit 30 may also be utilized to set initial parameters for the operation of the pulse generator 20, or to modify already-set parameters.

D. Remote Control.

The remote control 40 is used by the patient 12 to provide real-time, continuous feedback to the control unit 30 regarding how the patient 12 is responding to various stimuli. For example, the patient 12 may use the remote control 40 to indicate how the patient 12 is feeling at that time. By way of example, the patient 12 could use the remote control 40 to indicate pain levels. The control unit 30 may track and record the feedback from the patient 12 so as to improve the functionality of the pulse generator 20 as tuned to that particular patient's 12 needs.

As shown in FIGS. 2, 4, 6, and 8, a remote control 40 may be used by the patient 12 to provide feedback to electronic stimulation from the pulse generator 20 in real-time. This feedback may be stored and processed by the control unit 30 to create stimulation parameters that may be suited to that particular patient 12. The remote control 40 will generally be wirelessly connected to the control unit 30, such as through various wireless communications protocols such as Bluetooth or RF. The remote control 40 may also be configured to wirelessly connect to the pulse generator 20 through its antenna.

The shape, size, and configuration of the remote control 40 may vary in different embodiments. The remote control 40 will generally be of a size that will allow it to be hand-held. The remote control 40 may also be sized so as to easily fit within a pocket of the patient 12 in a manner that is not obstructive. For example, the remote control 40 will preferably not cause any discomfort for the patient 12 when running or jogging. In some embodiments as discussed below, the remote control 40 may be configured to be worn by the patient 12, or may be incorporated into a device the patient 12 already has, such as a phone or watch.

The remote control 40 may include a number of controls or other options. In the exemplary embodiment shown in the figures, a simplified remote control 40 is shown which includes only two inputs—a first input for positive feedback 41 and a second input for negative feedback 42. The inputs may be physical buttons, switches, or the like, or feedback may be entered via a touchscreen in some embodiments.

In other embodiments, the remote control 40 may be configured to respond to audible commands or feedback. Such an embodiment of the remote control 40 may be desirable in situations where patients 12 have extremely limited mobility, or lack the motor skills to hold the remote control 40 or interact with the feedback inputs of the remote control 40. For example, a patient 12 who has missing or disfigured hands may benefit from a remote control 40 configured to receive audible inputs.

In such embodiments, the remote control 40 may be configured to recognize a phrase from the patient 12 to indicate positive feedback and a second phrase from the patient 12 to indicate negative feedback. By way of example, the remote control 40 may be configured to process an audible statement of "I am in pain" as negative feedback 42 and an audible statement of "I feel fine" as positive feedback 41. It should be appreciated that the type of phrase used to activate the remote control 40 based on audible instructions may vary in different embodiments and thus should not be construed as limited by the exemplary phrases suggested above.

As shown throughout the figures, the remote control 40 will generally include an input for positive feedback 41 and an input for negative feedback 42. It should be appreciated that additional inputs may be present on the remote control 40. The figures merely illustrate only positive and negative feedback 41, 42 inputs for simplicity. It is possible, and in fact likely, that the remote control 40 will typically include inputs other than the positive and negative feedback 41, 42 inputs shown in the figures. For example, the remote control 40 could allow manual adjustment of stimulation parameters in some embodiments.

It should be appreciated that there are a wide range of types of remote controls 40 which may be utilized by the patient 12. The type of remote control 40 used may be selected based on the desires and needs of the particular patient 12. For example, a largely immobile patient 12 may benefit from a conventional remote control 40 such as shown in FIG. 2. A more active patient 12, such as a jogger, may benefit from a remote control 40 better-suited for exercise, such as a necklace 44 or smart watch 47.

FIGS. 2, 7A, 7B, 7C, and 7D illustrate exemplary embodiments of a remote control 40 for use with the method and system for automated neuromodulation through machine learning 10. FIG. 2 illustrates a first embodiment of the remote control 40 which has a conventional appearance similar to a standard television remote. Such an embodiment of the remote control 40 may be well-suited for immobile patients 12, or patients 12 who are conducting the training phase in a hospital environment. The exemplary embodiment of the remote control 40 shown in FIG. 2 is illustrated as comprising a positive feedback 41 input comprised of a happy (smiling) face and a negative feedback 42 input comprised of a sad (frowning) face.

Figure 7A:
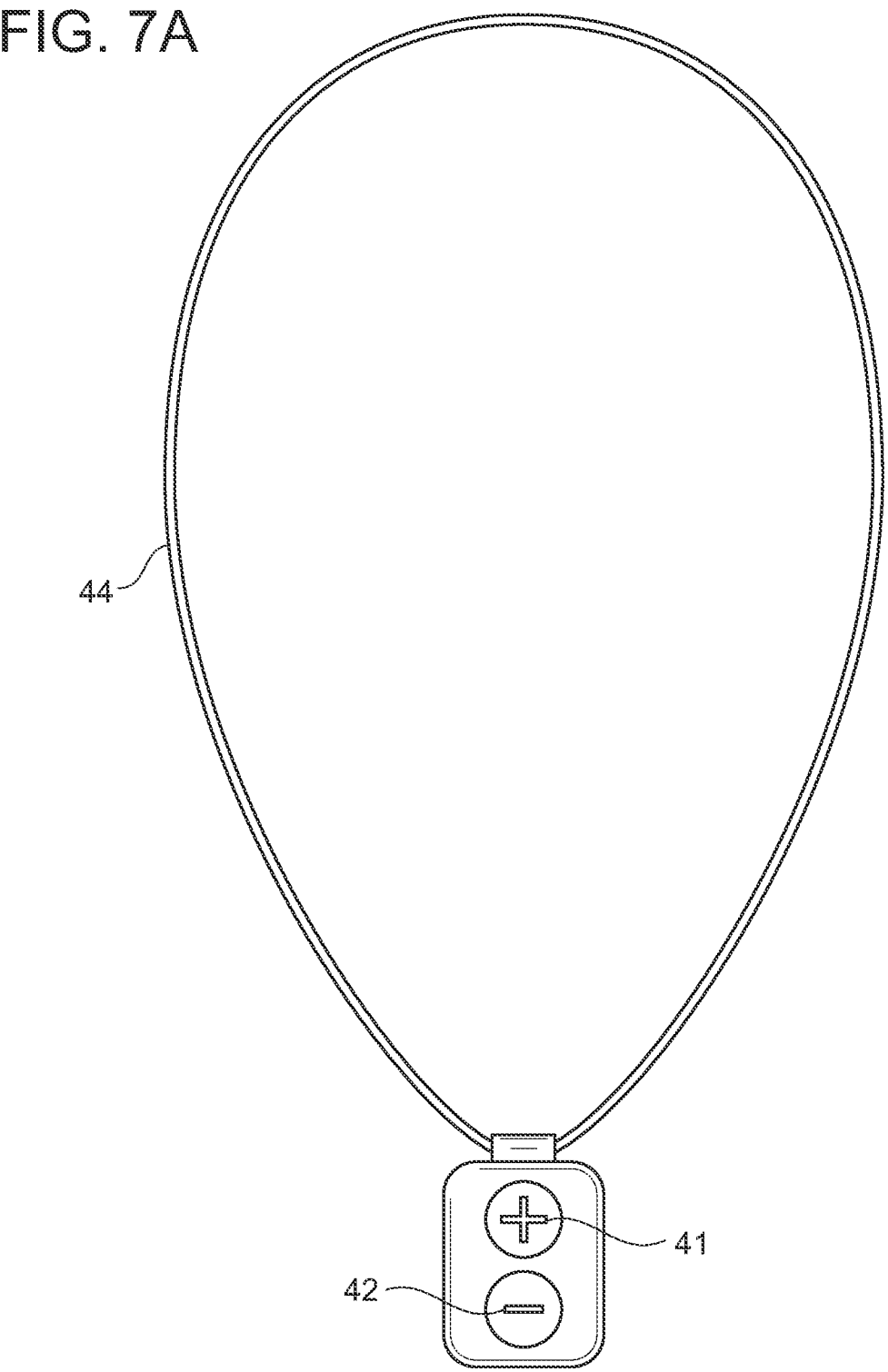
FIG. 7A is a frontal view of a remote control comprised of a necklace of a method and system for automated neuromodulation through machine learning in accordance with an example embodiment.

FIG. 7A illustrates another exemplary embodiment of a remote control 40 which is comprised of a necklace 44. The necklace 44 embodiment of the remote control 40 may be well-suited for mobile patients 12 who expect to travel or be generally "on-the-go". The necklace 44 embodiment of the remote control 40 shown in FIG. 7A is illustrated as comprising a positive feedback 41 input comprised of a "plus sign" (+) and a negative feedback 42 input is comprised of a "negative sign" (−).

Figure 7B:
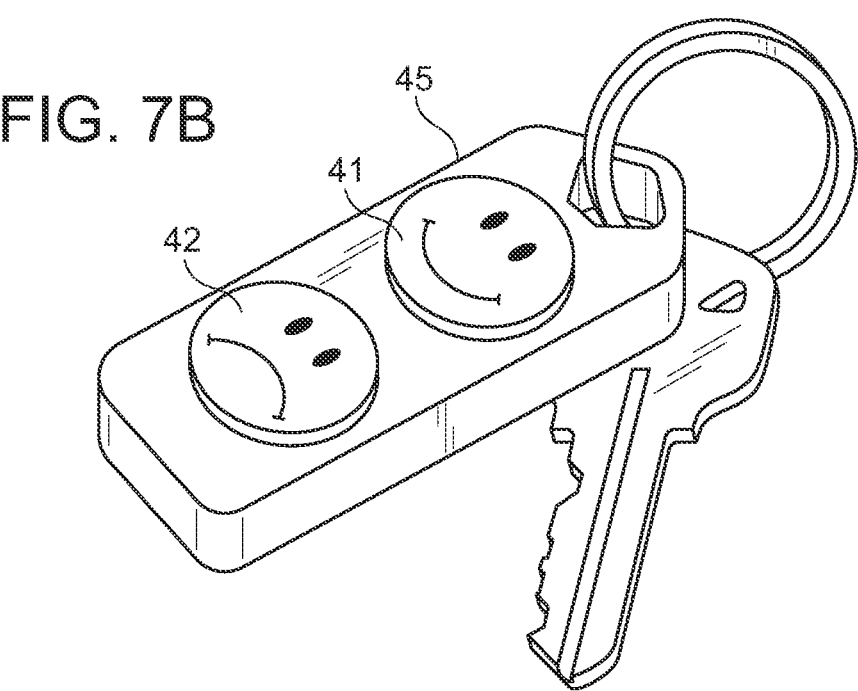
FIG. 7B is a frontal view of a remote control comprised of a key fob of a method and system for automated neuromodulation through machine learning in accordance with an example embodiment.

FIG. 7B illustrates yet another exemplary embodiment of a remote control 40 which is comprised of a key fob 45. The key fob 45 embodiment of the remote control 40 may be well-suited for patients 12 who expect to travel by vehicle regularly, or simply any patient 12 who desires a remote control 40 that may be stored on a key chain. The key fob 45 embodiment of the remote control 40 shown in FIG. 7B is illustrated as comprising a positive feedback 41 input comprised of a happy (smiling) face and a negative feedback 42 input comprised of a sad (frowning) face.

Figure 7C:
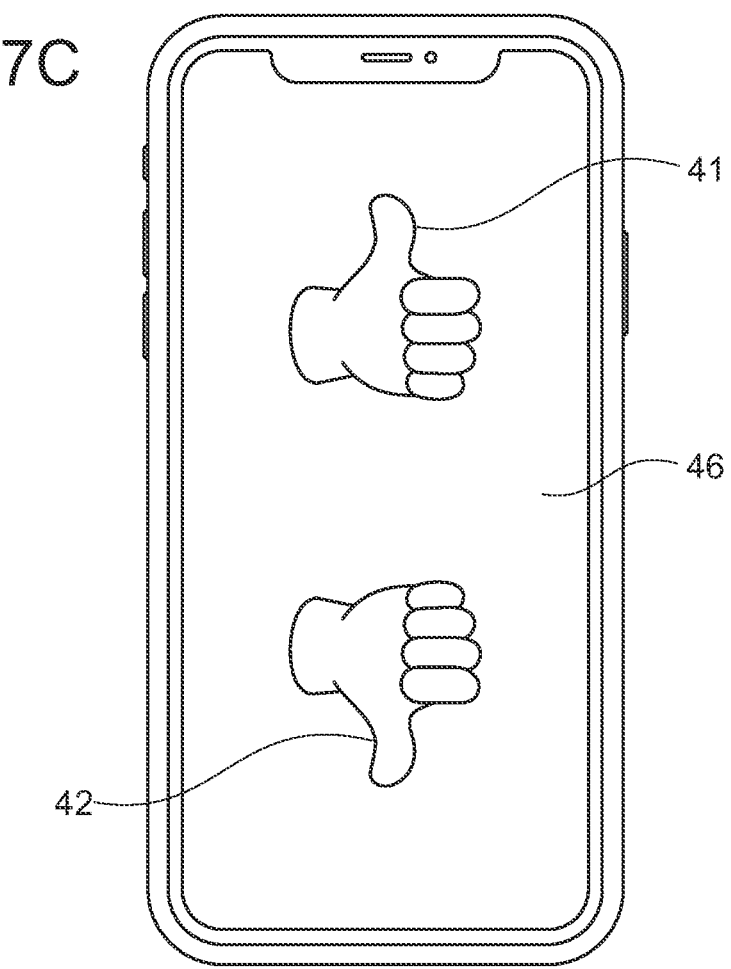
FIG. 7C is a frontal view of a remote control comprised of a mobile device of a method and system for automated neuromodulation through machine learning in accordance with an example embodiment.

FIG. 7C illustrates another exemplary embodiment of a remote control 40 which is comprised of a mobile device 46. The mobile device 46 may comprise a smart phone or the like. The mobile device 46 may operate various types of operating systems, such as but not limited to Android or IOS. The mobile device 46 may include a software application installed thereon which performs the functionality of the remote control 40. In the exemplary embodiment shown in FIG. 7C, the mobile device 46 is illustrated as comprising a positive feedback 41 input comprised of a "thumbs up" and a negative feedback 42 input comprised of a "thumbs down". As shown, the feedback inputs 41, 42 may comprise areas of a touchscreen when used on a mobile device 46 such as a smart phone.

Figure 7D:
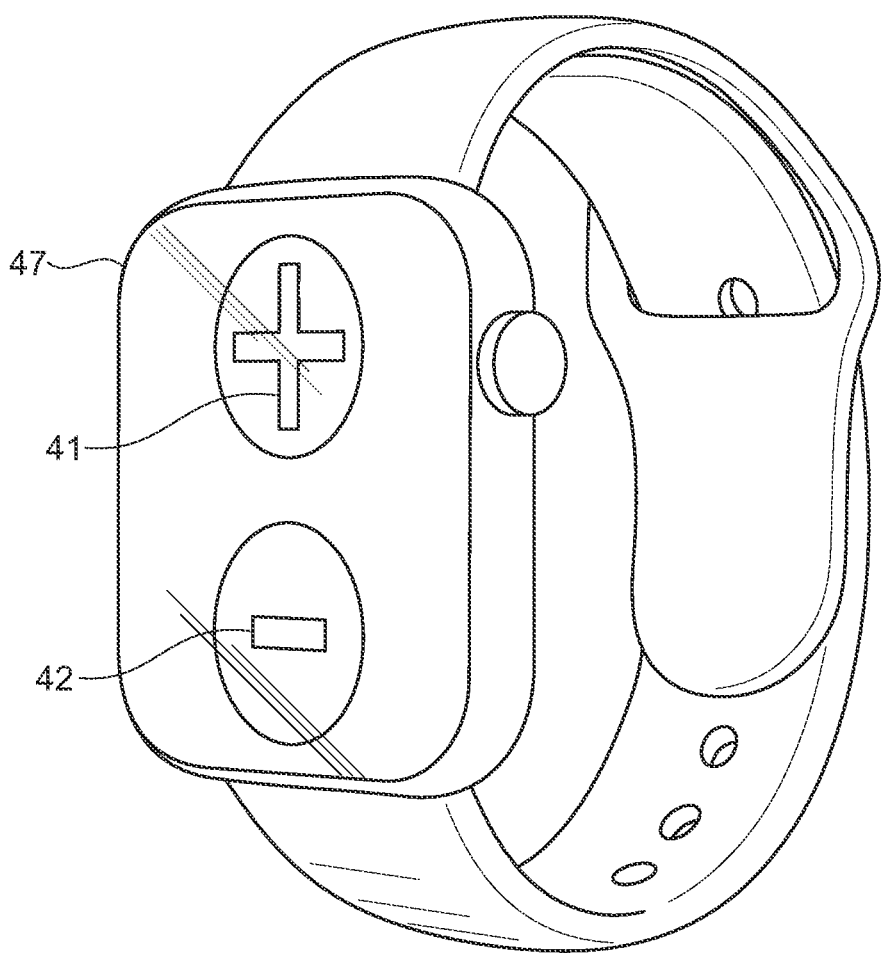
FIG. 7D is a perspective view of a remote control comprised of a smart watch of a method and system for automated neuromodulation through machine learning in accordance with an example embodiment.

FIG. 7D illustrates another exemplary embodiment of a remote control 40 which is comprised of a smart watch 47 or other wrist-worn mobile device. The smart watch 47 may comprise various types of wrist-worn mobile devices known in the art, including but not limited to Apple watches, Fitbits, and the like. The mart watch 47 may operate various types of operating systems, such as but not limited to Android or IOS. The smart watch 47 may include a software application installed thereon which performs the functionality of the remote control 40. In the exemplary embodiment shown in FIG. 7D, the smart watch 47 is illustrated as comprising a positive feedback 41 input comprised of a "plus sign" (+) and a negative feedback 42 input that is comprised of a "negative sign" (−).

As shown with each of the exemplary embodiments of a remote control 40 discussed above, each embodiment of the remote control 40 will generally include a positive feedback 41 input and a negative feedback 42 input. The positive feedback 41 input will be comprised of an input to indicate to the control unit 30 that the patient 12 is feeling good, or responding positively to the current stimuli being applied. The negative feedback 41 input will be comprised of an input to indicate to the control unit 30 that the patient 12 is not feeling goods, is feeling pain, or is responding negatively to the current stimuli being applied.

This feedback will be used by the control unit 30 to create or update existing stimulation parameters which are fine-tuned to that particular patient 12, taking into account other considerations such as activities of the patient 12, whether the patient 12 is standing, sitting, or walking, the orientation of the patient 12, or other factors.

The feedback 41, 42 input may be entered in various manners by the patient 12. For example, the patient 12 may press a tactile button or touchscreen to provide positive or negative feedback 41, 42. In other embodiments, the patient 12 may vocally state one or more preset phrases such as "I feel good" or "I feel bad" that serve as the input for positive or negative feedback 41, 42.

In yet other embodiments, patient 12 feedback may be motion or movement based. The patient 12 may make preset motions or movements with the remote control 40 such that the remote control 40 or control unit 30 may translate those preset motions or movements into positive or negative feedback 41, 42.

For example, the patient 12 may set the remote control 40 to register positive feedback 41 if the remote control 40 is shaken vertically and to register negative feedback 42 if the remote control 40 is shaken horizontally. Such an embodiment may be desirable for patients 12 who lack the fine motor skills to enter feedback via inputs on the remote control 40 and are unable to speak. In such embodiments, the remote control 40 may include a sensor 24 such as a gyroscope and/or accelerometer as is common with many modern mobile devices 46 so that the remote control 40 can recognize the motions.

E. Central Database.

The method and system for automated neuromodulation through machine learning 10 may include a central database 52 which acts as repository of data collected from numerous patients 12. The central database 52 may be utilized to continually receive and process data from patients 12 with pulse generators 20. Such data may include feedback data from the various patients 12 at various times. The data may also include data to identify the position, orientation, and activities of each patient 12 at the time of the feedback. All of this information may be collated in the central database 52 so as to create a standardized stimulation protocol that may act as a baseline on future patients 12.

The central database 52 will generally be comprised of memory which stores the data discussed above. The central database 52 may be remotely accessed by various control units 30 through a communications network, such as the Internet. The central database 52 may in some embodiments be incorporated into the control unit 30. In other embodiments, the control unit 30 may communicate with the central database 52.

Figure 6:
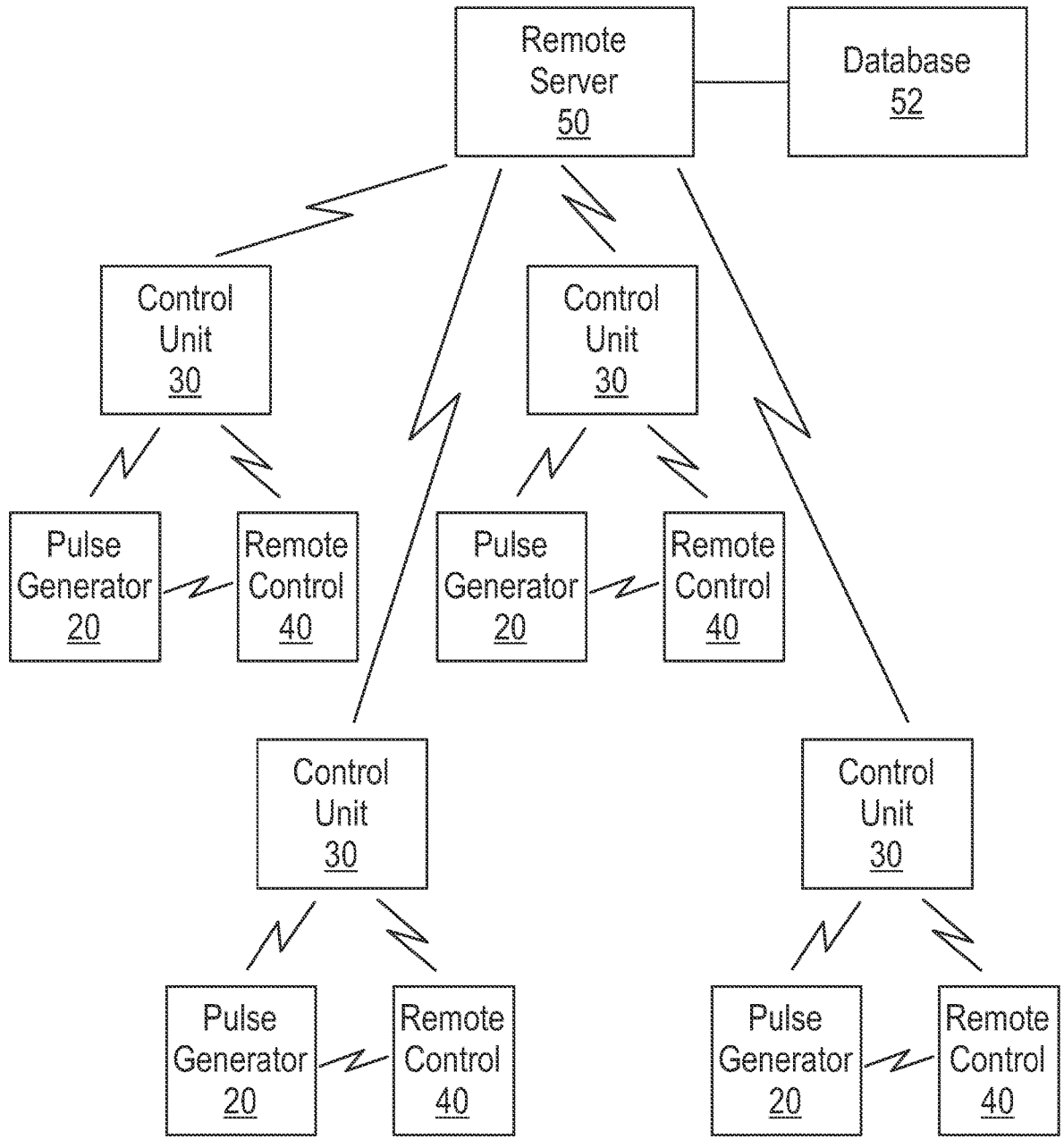
FIG. 6 is a block diagram of a method and system for automated neuromodulation through machine learning in accordance with an example embodiment.

FIG. 6 illustrates an exemplary system 10 which includes a central database 52. As can be seen in FIG. 6, the central database 52 is stored on a remote server 50. The remote server 50 may comprise a computer system including a processor and memory which stores the central database 52. The remote server 50 is illustrated as being communicatively interconnected with the control unit 30. The control unit 30 will transfer various data to the remote server 50, including data related to which levels of stimulus are effective on a particular patient 12.

Using this information, the remote server 50 and/or control unit 30 may utilize machine learning algorithms to fine-tune stimulation criteria for a particular patient 12. Further, as discussed below, the remote server 50 may create a baseline stimulation criteria which may be applied universally upon the start of the training phase, with the baseline stimulation criteria being subsequently tailored to the particular patient 12 during the course of the training phase based on patient 12 feedback.

Continuing to reference FIG. 6, it can be seen that the control unit 30 is communicatively interconnected with the pulse generator 20, the remote control 40, and the remote server 50. The control unit 30 will control operation of the pulse generator 20, causing the pulse generator 20 to automatically apply stimulus based on the baseline stimulation criteria or the patient-tailored criteria, whichever is available at the time. As the pulse generator 20 is used for a particular patient 12, the system 10 will fine tune the stimulation criteria to match the needs and feedback of that particular patient 12. This fine tuning will occur in earnest during the training phase, but may continue even after the training phase to accommodate the changing needs or circumstances of the patient 12.

The control unit 30 is also communicatively interconnected with the remote control 40 so as to receive positive feedback 41 or negative feedback 42 which is used to fine tune the stimulation criteria for that particular patient 12. This data may also be transferred to the central database 52, such as on the remote server 50, where it may be stored to inform any changes to the baseline stimulation criteria. The data may be anonymized when stored on the central database 52 to comply with privacy laws such as HIPAA.

Figure 4:
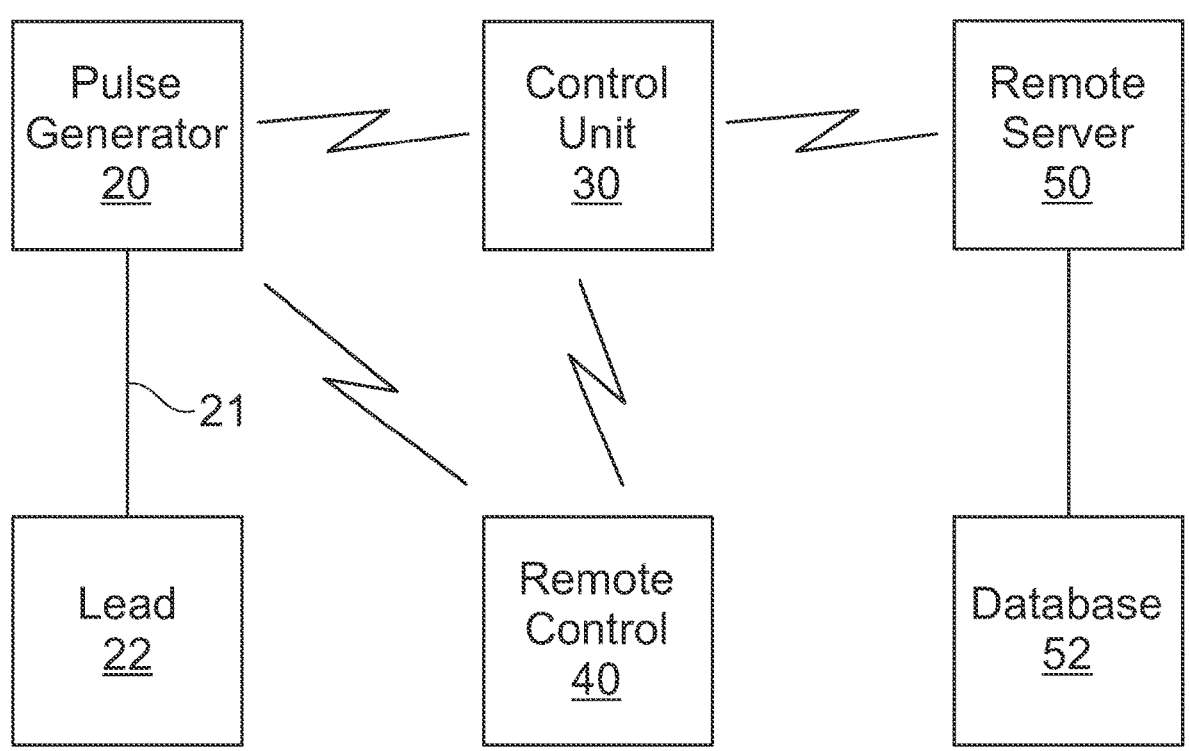
FIG. 4 is a block diagram of a method and system for automated neuromodulation through machine learning in accordance with an example embodiment.

The pulse generator 20 is communicatively interconnected as shown in FIGS. 2 and 4 with the control unit 30 so as to receive stimulation instructions from the control unit 30. The control unit 30 will operate under either the baseline criteria or the fine-tuned criteria depending on the amount of time that the patient 12 has been using the system 10. The pulse generator 20, after training, will function independently and automatically to provide electrical stimulation based on the needs and past feedback from the patient 12.

FIG. 6 illustrates an exemplary system 10 in which data from multiple patients 12 may be collected into a central database 52. As shown in FIG. 6, a plurality of control units 30 are each communicatively interconnected to a remote server 50. Each of the control units 30 is communicatively interconnected with a pulse generator 20 of a patient 12 and a remote control 40 which is controlled by that patient 12 to provide positive feedback 41 or negative feedback 42 to various electric stimuli.

While FIG. 6 illustrates the connection of four independent control units 30 to the remote server 50, it should be appreciated that many, many more control units 30 may be connected to the remote server 50 to transfer data thereto. The systems and methods described herein may function with any number of control units 30. In fact, the more control units 30 (and thus patients 12) connected to the system will improve the machine learning to improve the baseline criteria.

All data received from the control units 30 is stored in the central database 52, in anonymized format to protect identities of the patients 12. This data may include any feedback 41, 42 from the patient 12 as well as sensor 24 data at the time of feedback 41, 42, such as but not limited to the positioning, orientation, and movement of the patient 12 at the time of feedback 41, 42. As discussed below, this data may be used by the remote server 50 to formulate a baseline criteria to be applied to all patients 12 such that each of the pulse generators 20 in the embodiment of FIG. 6 may function automatically for each specific patient 12.

F. Operation of Preferred Embodiment.

Figure 8:
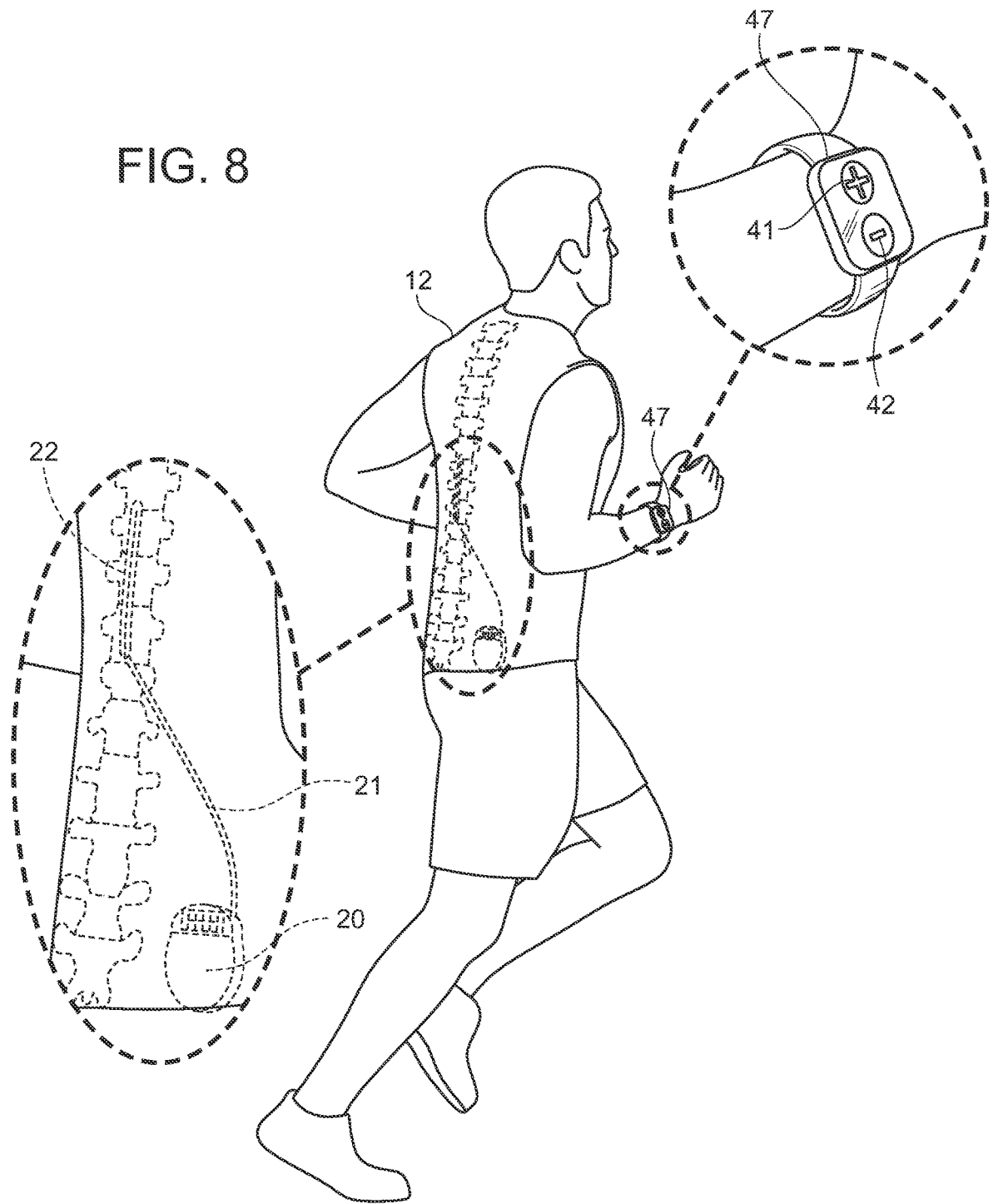
FIG. 8 is a perspective view of a patient using a method and system for automated neuromodulation through machine learning in accordance with an example embodiment.

In use, the lead 22 is first implanted into the patient 12. The pulse generator 20 may be implanted into the patient 12 with the lead 22, or may be kept external to the body of the patient 12 while maintaining communication with the lead 22. FIGS. 1 and 8 illustrate an exemplary embodiment in which the pulse generator 20 has been implanted near the hips of the patient 12. It should be appreciated, however, that the pulse generator 20 may be positioned at various locations in the body or outside of the body of the patient 12 and thus should not be construed as limited to any particular location such as that shown in FIG. 1.

The pulse generator 20 will generally include one or more leads 22 which are connected to electrically stimulate one or more nerves of the patient 12, such as in or near the spine of the patient 12. In cases in which the pulse generator 20 is a distance from the desired nerve(s), an insulated extension wire 21 may be used to connect the pulse generator 20 to the leads 22 at the electric stimulation site. In such an embodiment, both the pulse generator 20 and the leads 22 are implanted within the body of the patient 12. In other embodiments, the pulse generator 20 may be in communication with, but not directly connected to, the leads 22. In such embodiments, the pulse generator 20 may be in communication with the leads 22, such as through radio frequency.

With the pulse generator 20 installed, an initial set up may be performed by a healthcare professional such as a nurse to initially configure the pulse generator 20. The pulse generator 20 will be connected to both the control unit 30 and the remote control 40. The healthcare professional may inquire about some baseline statistics from the patient 12 which may be entered into the control unit 30 to create a baseline stimulation protocol. If connected to a central database 52 including data from other patients 12, that data may be utilized and incorporated by the control unit 30 to determine the initial, baseline stimulation criteria.

With the pulse generator 20 installed and active, the training phase of the system 10 may begin. During the training phase, the system 10 will continuously receive patient feedback 41, 42 through the remote control 40 to indicate how the patient 12 is responding to certain situations or stimulation levels. Using this patient feedback 41, 42 along with accompanying sensor 24 data indicating the position, orientation, and movement of the patient 12 at the time of feedback 41, 42, the control unit 30 will formulate an automated stimulation protocol that is tailored to that specific patient's 12 needs.

The training phase will generally begin soon after the pulse generator 20 has been implanted in the patient 12. During the training phase, the control unit 30 will automatically run a number of different stimulation programs comprised of different electrical stimuli being applied at different strengths and at different times. The patient 12 will then provide binary feedback 41, 42 indicating to the control unit 30 how the patient 12 is responding to the specific stimulus being applied. This data will be retained by the control unit 30 to formulate an automated stimulation protocol based on machine learning.

During the training phase, the patient 12 may be prompted to perform various maneuvers or actions. During each of the maneuvers or actions, the control unit 30 will direct various levels of electrical stimulation to the patient 12 via the pulse generator 20. The patient 12 will provide feedback 41, 42 throughout the training phase so that the control unit 30 may continue to learn what electrical stimulation protocol is best-suited for that particular patient 12.

By way of example, the control unit 30 may prompt the patient to walk around the room. As the patient 12 is walking around the room, the control unit 30 will direct different levels of electrical stimulation to be applied to the patient 12 via the pulse generator 20. The patient 12 will provide real-time feedback 41, 42 using the remote control 40. When the feedback 41, 42 is received by the control unit 30, the control unit 30 will make note of the activities being performed by the patient 12 at that time, including positioning, orientation, and movement of the patient 12. This data will be used by the control unit 30 to keep track of activities which require more stimulation and activities which may require less or even no stimulation for that particular patient 12.

The activities that the patient 12 performs during the training phase may vary in different embodiments. By way of example, the patient 12 may be prompted to walk, sit, stand, run, jump, lay down, sit up, jog, lift items, lower items, and various other common activities that a patient 12 may perform in their day-to-day life.

The training phase may be personalized to the particular patient 12. For example, a wheelchair-bound patient 12 may be prompted to make certain maneuvers with his/her wheelchair. A patient 12 with a history of running triathlons will have a completely different training session, in which high exercise activities tested since that particular patient 12 is likely to be performing vigorous exercises using the pulse generator 20 for pain management. Throughout the training phase, different levels of electrical stimulation will be applied by the pulse generator 20 to determine patient 12 response to different stimulation during different activities or situations.

The control unit 30 may also utilize the sensor 24 to identify that the patient 12 is performing actions that should be tested. For example, if the control unit 30 detects that the patient 12 is walking around, electrical stimuli may be applied to gauge patient 12 feedback at that time. Thus, using the sensor 24, the control unit 30 may take data readings even without separately prompting the patient 12 to perform a specific activity. Instead, the control unit 30 can incorporate its testing into the actual day-to-day activities of the patient 12 during the training phase.

During the training phase, it is important that the patient 12 continuously provides feedback 41, 42 so that the control unit 30 can learn an optimal, automated stimuli protocol for that particular patient 12. In some embodiments, the patient 12 may be prompted to provide feedback 41, 42 at certain times. The remote control 40 may provide such prompts. For example, the remote control 40 may light up, vibrate, or emit audible sounds or alarms if the patient 12 is overdue for providing feedback 41, 42.

Feedback 41, 42 will be requested frequently during the training phase, and far less frequently after the training phase has been completed. The amount of time allowed to pass between feedback 41, 42 from the patient 12 may vary in different embodiments. For example, the control unit 30 may be configured to prompt the remote control 40 to request feedback 41, 42 from the patient 12 every fifteen minutes during the training phase.

Other time periods may be utilized. At the conclusion of the training phase, when the control unit 30 has created a protocol for that particular patient 12 based on feedback 41, 42, the patient 12 will not be required to provide feedback 41, 42 with near the same frequency. For example, after the training phase has been completed, the patient 12 may only be prompted for feedback once per quarter.

The duration of the training phase will vary in different embodiments. By way of example and without any limitation, the training phase could last for the first 4-6 weeks that the patient 12 is fitted with the pulse generator 20. However, it should be appreciated that less time may be necessary if the control unit 30 is able to formulate the protocol for that patient 12 in a faster time period. For example, a patient 12 who is frequently providing feedback 41, 42 will complete his/her training phase faster than a patient 12 who is less consistent with providing feedback 41, 42 to the control unit 30. Eventually, the system 10 will function without any requirement for feedback 41, 42 from the patient 12 at all.

During the training phase, the control unit 30 will continuously monitor patient 12 feedback 41, 42 along with accompanying sensor 24 readings to determine an optimal stimulation protocol for that particular patient 12. The control unit 30, upon completing the protocol, may transfer the protocol to the pulse generator 20 so that the pulse generator 20 may automatically function independent from the control unit 30.

For example, the control unit 30 may transfer an electrical stimulation protocol which includes various criteria for various levels of electrical stimulation to be applied to the patient 12. If a particular patient 12 experiences severe pain when standing up, then the pulse generator 20 will be instructed by the control unit 30 to provide an appropriate level of stimulation any time that the sensor 24 detects the patient 12 going from a sitting position to a standing position. If that same patient 12 does not typically experience pain levels when sitting down, the pulse generator 20 will similarly be programmed not to provide any stimulation when the sensor 24 detects the patient 12 going from a standing position to a sitting position.

The control unit 30 may be communicatively connected to a central database 52 which collects data from a large number of patients 12 to create a baseline universal criteria and protocol for treatment of patients 12 with implanted pulse generators 20. In such an embodiment as shown in FIG. 6, each patient 12 fitted with a pulse generator 20 communicates data to the central database 52, which may be stored on a remote server 50.

The remote server 50 then processes the data from all of the patients 12 to formulate the baseline protocol and criteria which may be automatically applied by all of the pulse generators 20 prior to the training phase, with the training phase informing adjustments made to the baseline protocol and criteria to match a specific, unique patient 12. The baseline protocol and criteria may include levels and periods of stimulation which are based on body position, body activity, time of day, or situation.

The data transmitted to and processed by the remote server 50 may include a wide range of information relating to the electrical stimulation applied, the patient 12 him/herself, and other characteristics. By way of example and without limitation, patient 12 data may include types of symptoms, locations of lead 22 placement, age, race, sex, medical diagnosis, and body habitus. All of this data from a wide range of patients 12 may be stored on the central database 52 and processed to create the baseline protocol and criteria to be applied to a new patient 12. As more patients 12 use the system, the baseline criteria and protocol will be improved as more data is collected and processed. All data may be anonymized to comply with privacy laws such as HIPAA.

After the training phase has been completed, the pulse generator 20 will be configured to automatically apply an electrical stimulation protocol and criteria to the patient 12. This protocol and criteria will have been formulated by the control unit 30 and/or remote server 50 and may take into account feedback and related data from any other patients 12 using the system 10. The protocol and criteria may take into account any of the factors discussed above, including but not limited to symptoms, locations of lead 22 placement, age, race, sex, medical diagnosis, and body habitus.

The protocol and criteria will be used by the pulse generator 20 to determine when to apply electrical stimulation via the pulse generator 20 and what level of electrical stimulation to apply. For example, if during the training phase the patient 12 encountered significant pain while sitting dormant, the pulse generator 20 will automatically apply an electrical stimulation when the patient 12 is detected by the sensor 24 to be sitting dormant.

The level of electrical stimulation to be applied will be informed by the range of electrical stimulation levels which the patient 12 had previously responded to with positive feedback 41 on the remote control 40 during the training phase when sitting dormant. In this manner, the pulse generator 20 may learn to anticipate situations where electrical stimulation would be favorable for the patient 12 and, further, the level of electrical stimulation to apply in different situations, times of day, locations, etc.

Figure 9:
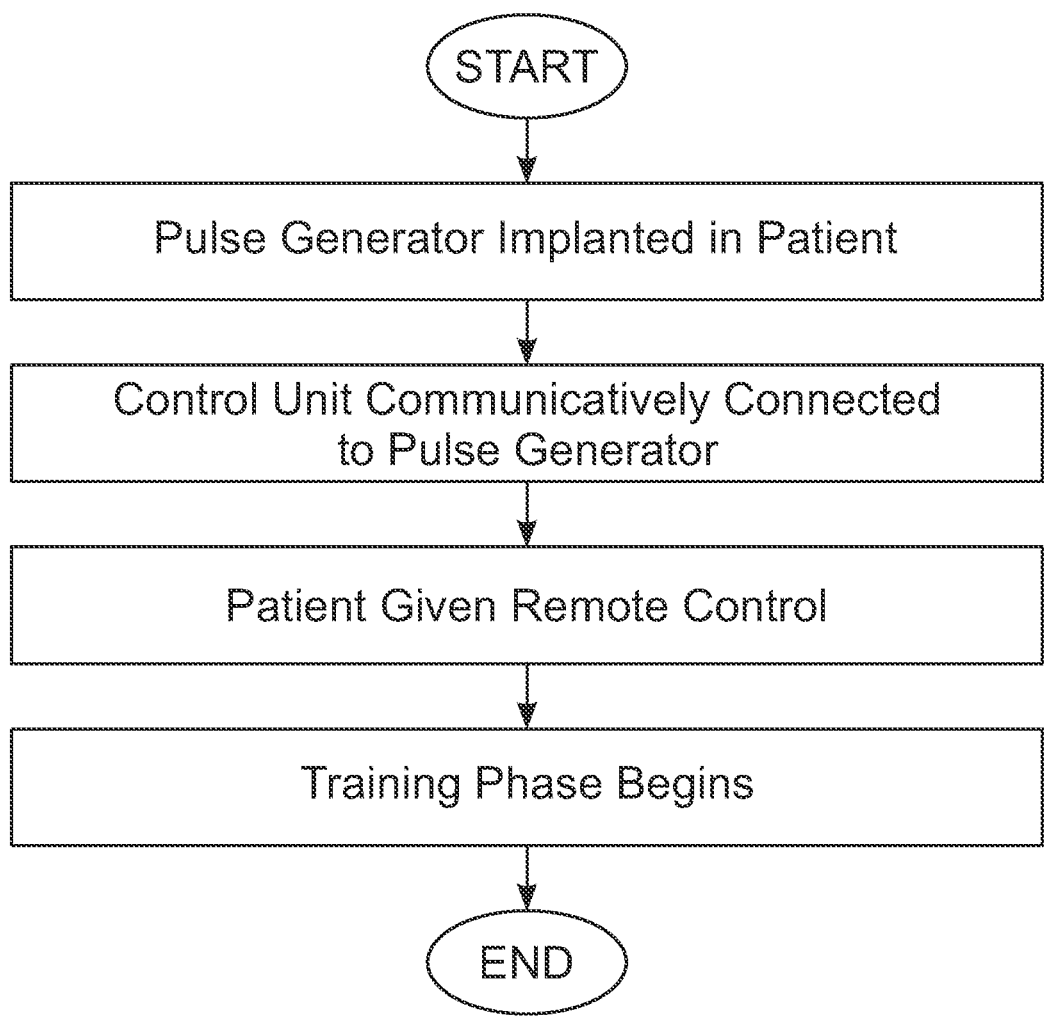
FIG. 9 is a flowchart illustrating pulse generator implantation of a patient of a method and system for automated neuromodulation through machine learning in accordance with an example embodiment.

FIGS. 9-20 are exemplary flowcharts illustrating various methods performed by the system 10 described herein. As shown in FIG. 9, the lead 22 may first be implanted into the patient 12. As discussed previously, the location and method of implantation of the lead 22 may vary in different embodiments. The pulse generator 20 will generally be implanted in a desirable location, such as near the hips of the patient 12, with an extension wire 21 being used to connect the leads 22/electrodes to the relevant nerve(s) of the patient 12. In other embodiments, however, the pulse generator 20 may instead be external to the body of the patient 12, with only the leads 22 being implanted. In such embodiments, the pulse generator 20 may be in communication with the leads 22, such as through wireless communication.

After the pulse generator 20 has been installed and the leads 22 connected to the relevant nerve(s), the control unit 30 may be communicatively connected to the pulse generator 20. In this manner, the control unit 30 may receive data from the pulse generator 20, such as the sensor 24. The control unit 30 may also transmit data to the pulse generator 20, such as instructions for application of electrical stimulus, including the duration and level of stimulus to be applied at any given time.

The patient 12 is given a remote control 40, which as discussed previously may be comprised of a necklace 44, key fob 45, mobile device 46, smart watch 47, or the like. A training phase will then commence during which the patient 12 will be prompted to perform a number of tasks or activities and indicate via the remote control 40 whether they are positively or negatively responding to any electrical stimulation (or lack of electrical stimulation) being applied.

Figure 10:
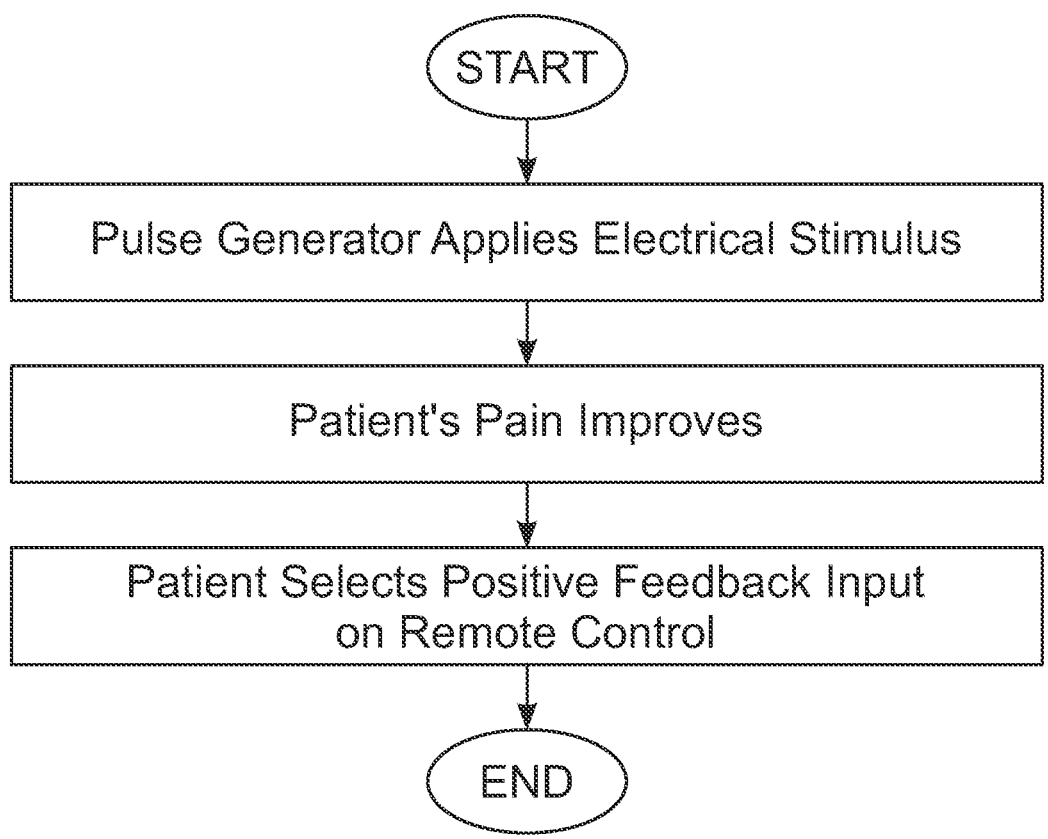
FIG. 10 is a flowchart illustrating patient positive feedback of a method and system for automated neuromodulation through machine learning in accordance with an example embodiment.
Figure 11:
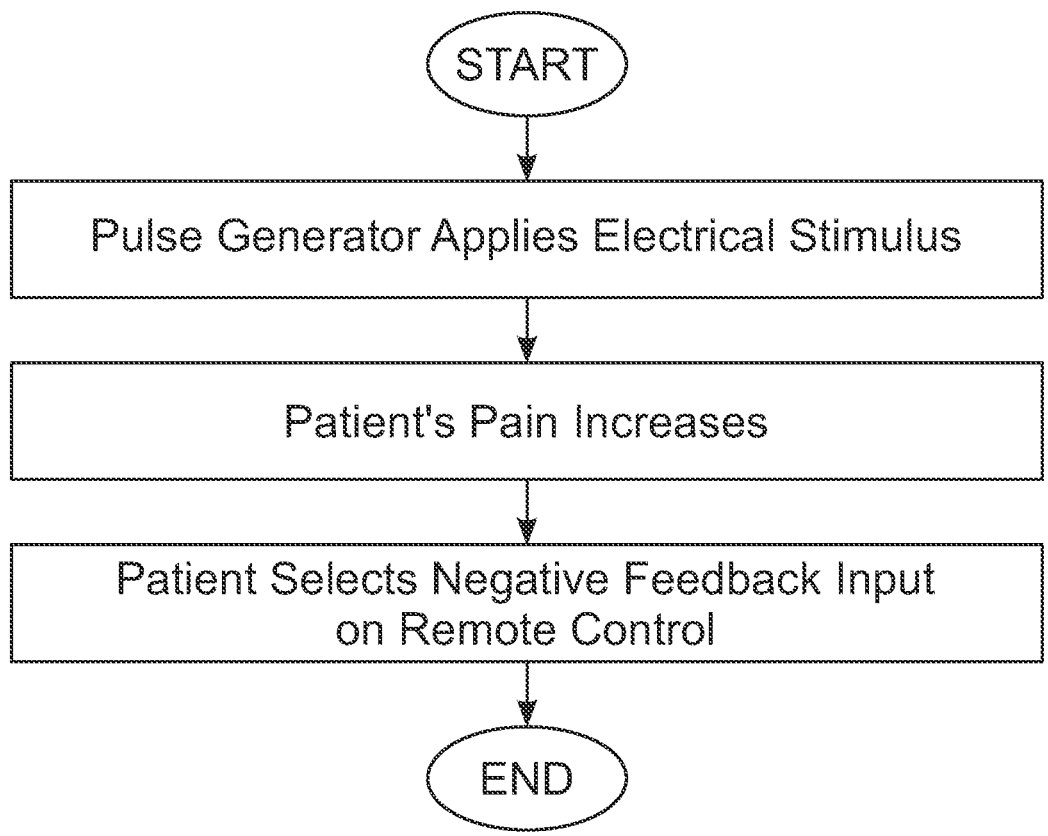
FIG. 11 is a flowchart illustrating patient negative feedback of a method and system for automated neuromodulation through machine learning in accordance with an example embodiment.

FIGS. 10 and 11 illustrate a simplified method of providing patient feedback. As shown in FIGS. 10 and 11, after the pulse generator 20 has applied electrical stimulation to the nerve(s), the patient 12 may select the positive feedback 41 input on the remote control 40 if the patient's 12 pain is improved or reduced. The patient 12 may select the negative feedback 42 input on the remote control 40 if the patient's 12 pain is increased upon application of the electrical stimulation to the nerve(s).

The pulse generator 20 and/or control unit 30 will collect data relating to how the patient 12 responded to certain levels of electronic stimulus during different situations or activities. This information will be used to train the system 10 via machine learning to automatically apply electrical stimulus to the patient 12 based on fine-tuned criteria and protocols.

Similarly, the patient 12 may indicate when pain has increased in an absence of electrical stimulation. For example, if the patient 12 is in considerable pain, the patient 12 in the absence of electrical stimulation, the patient 12 may select the negative feedback 42 input on the remote control 40. The pulse generator 20 will then apply a level of electrical stimulation to the patient 12. The patient 12 may then provide further feedback to indicate if the pain has improved, or gotten worse.

Figure 12:
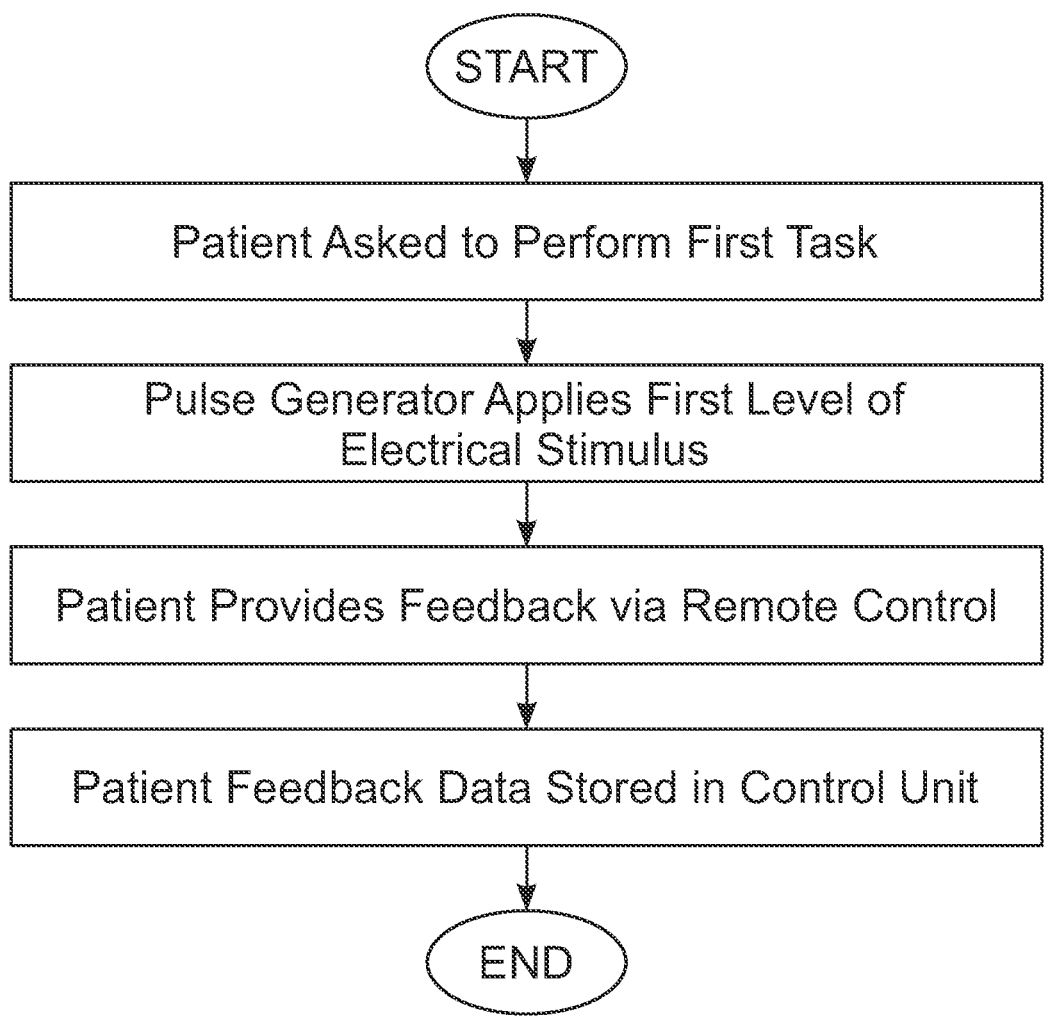
FIG. 12 is a flowchart illustrating the training phase of a method and system for automated neuromodulation through machine learning in accordance with an example embodiment.
Figure 13:
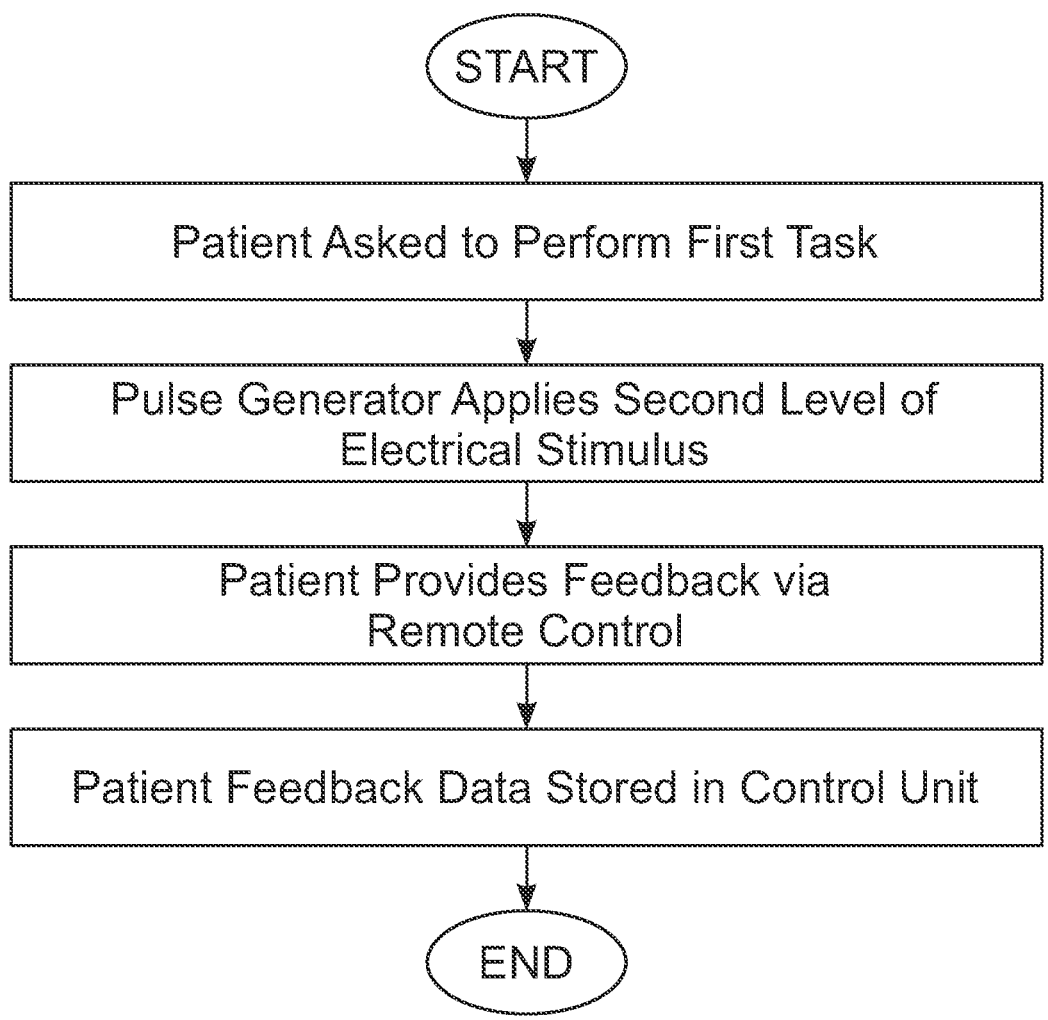
FIG. 13 is a flowchart illustrating the training phase of a method and system for automated neuromodulation through machine learning in accordance with an example embodiment.

FIGS. 12-16 illustrate exemplary methods of machine learning during the training phase. As shown in FIG. 12, the patient 12 may be asked to perform a first task. The task may include a wide range of activities, such as but not limited to sitting, standing, walking, leaning, laying down, jogging, stretching, flexion and extension of the spine, flexion and extension of a limb or joint, or any other activity which the patient 12 is likely to encounter in day-to-day life.

The activities which the patient 12 will be prompted to perform during the training phase may be customized to the particular patient 12. For example, if the patient 12 is immobile, the patient 12 will be prompted to perform tasks which are similarly immobile, such as laying down in various positions. If the patient 12 is an athlete, the patient 12 will be prompted to perform the exercises or activities which the patient 12 expects to perform during their day-to-day life after leaving the treatment center.

As the patient 12 performs the first task, the pulse generator 20 will apply a first level of electrical stimulation. The patient 12 will then provide feedback via the remote control 40 by selecting either the positive feedback 41 input or the negative feedback 42 input. The patient feedback data may be stored in the control unit 30. The patient feedback data may include a wide range of information, including but not limited to the time of day, activity being performed by the patient 12, the orientation of the patient 12, the speed of movement of the patient 12, the location that the leads 22 are installed, the symptoms of the patient 12, and the like.

The patient 12 may then be prompted to perform the same task again, during which the pulse generator 20 will apply a second level of electrical stimulation. The second level of electrical stimulation may be greater than or lesser than the first level of electrical stimulation. The period of the second level of electrical stimulation may be longer or shorter than the period of the first level of electrical stimulation. In any case, the patient 12 will then provide feedback via the remote control 40 by selecting either the positive feedback 41 input or the negative feedback 42 input.

Figure 14:
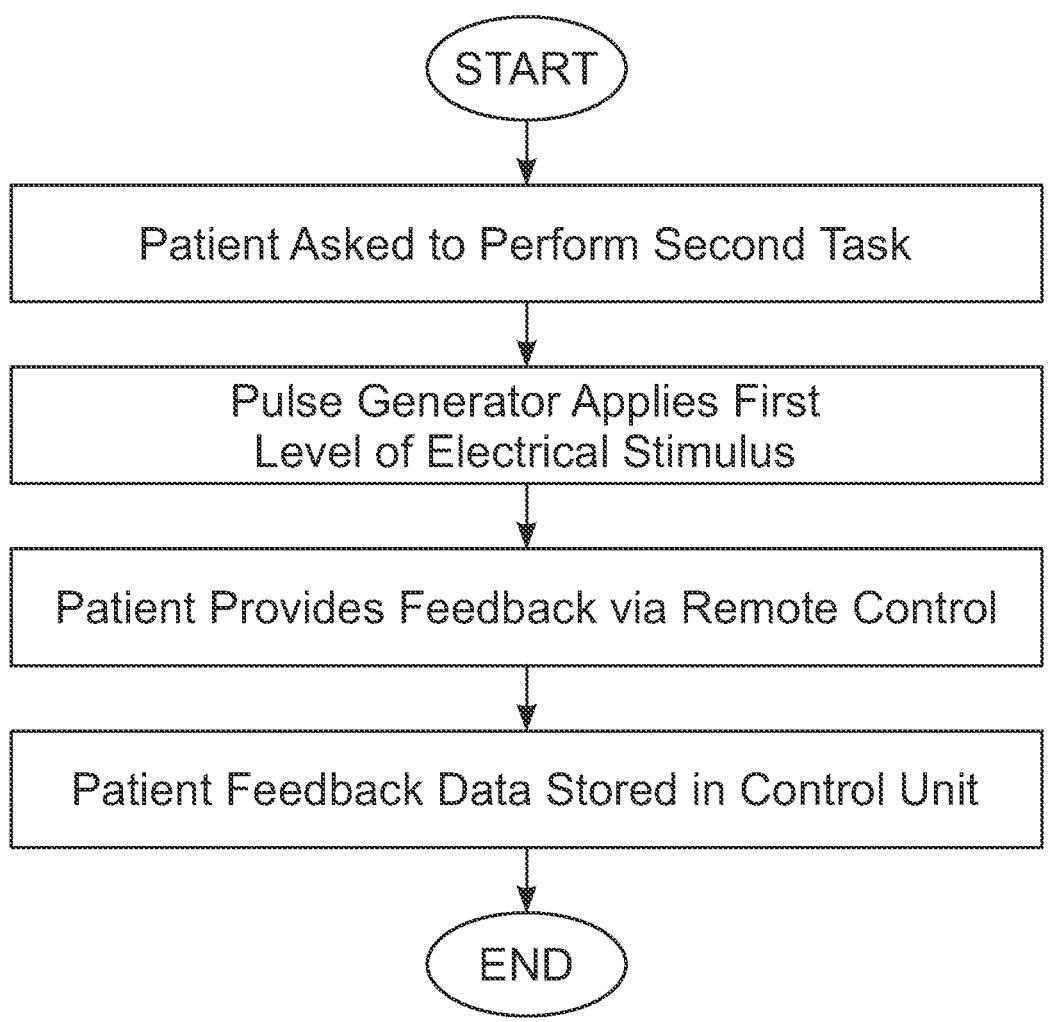
FIG. 14 is a flowchart illustrating the training phase of a method and system for automated neuromodulation through machine learning in accordance with an example embodiment.

As shown in FIG. 14, the patient 12 may then be prompted to perform a second task, with the second task being different from the first task. For example, if the first task was to sit dormant, the second task may be to walk around a room. As the second task is being performed by the patient 12, the pulse generator 20 applies a first level of electrical stimulation. The patient 12 will then provide feedback via the remote control 40 by selecting either the positive feedback 41 input or the negative feedback 42 input. The patient feedback data will be stored in the control unit 30 and collated with earlier data to continue to formulate a fine-tuned electrical stimulation protocol and criteria based on machine learning.

Figure 15:
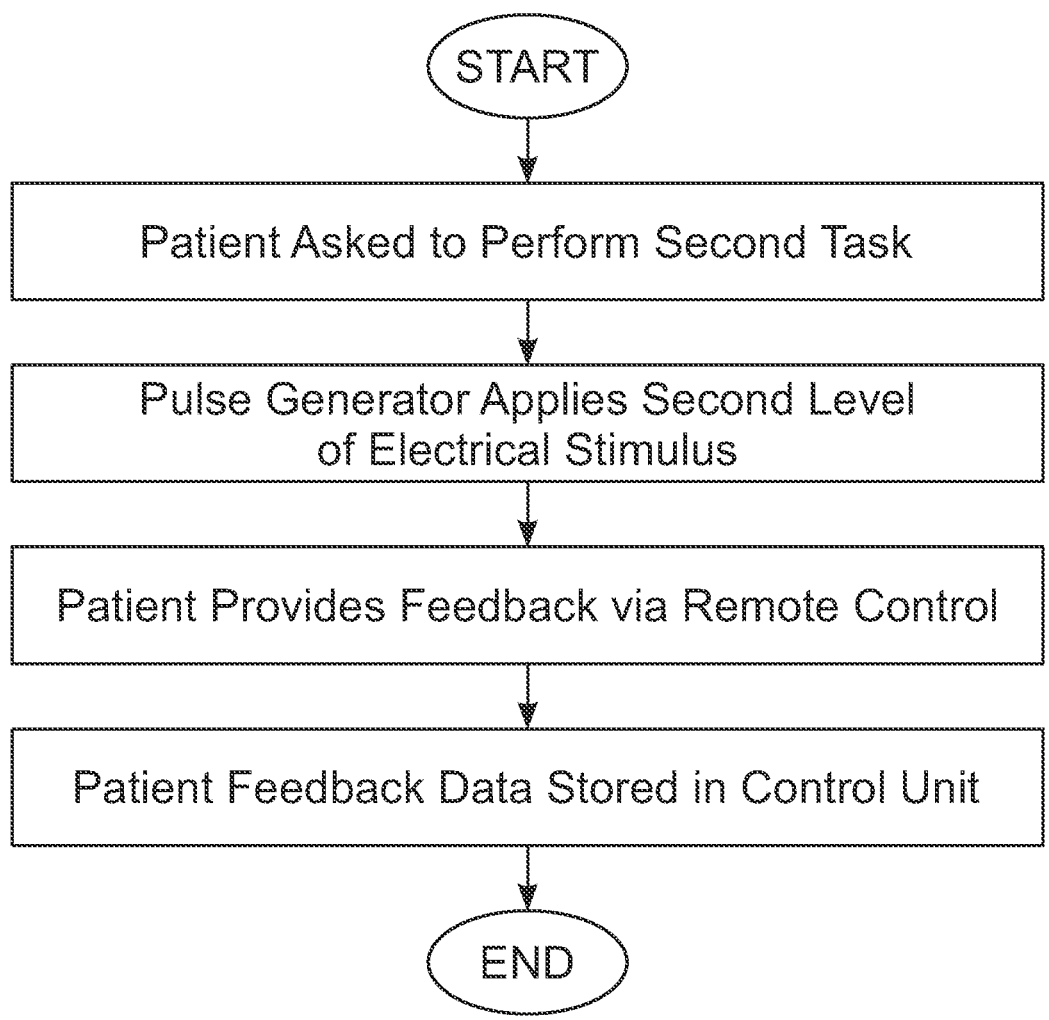
FIG. 15 is a flowchart illustrating the training phase of a method and system for automated neuromodulation through machine learning in accordance with an example embodiment.

As shown in FIG. 15, the patient 12 may then be prompted to perform the second task again, with a second level of electrical stimulation being applied by the pulse generator 20. The patient 12 will again provide feedback via the remote control 40, and the patient feedback data will be stored in the control unit 30 for further processing to formulate the electrical stimulation protocol and criteria for that particular patient 12.

Figure 16:
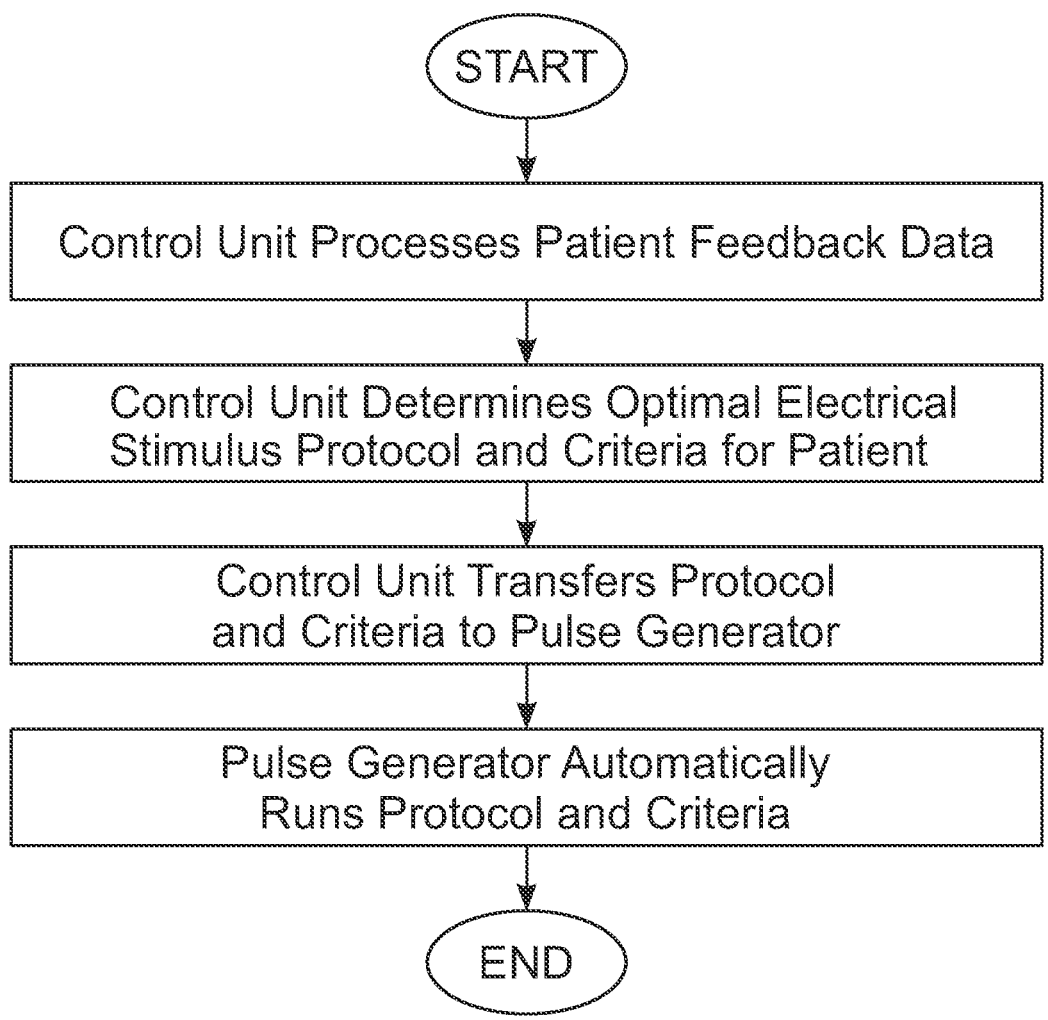
FIG. 16 is a flowchart illustrating pulse generator automation of a method and system for automated neuromodulation through machine learning in accordance with an example embodiment.

As shown in FIG. 16, the control unit 30 may be adapted to process all of the patient feedback data. While the above paragraphs describe two tasks being performed by the patient 12 at two different levels of electrical stimulation, it should be appreciated that the description is merely for exemplary purposes. In actual practice, it is likely that many, many more tests will be administered to the patient 12 during the training phase.

The patient feedback data will be stored in the control unit 30. As more data points are collected by the control unit 30, the control unit 30 will process the data point and, through machine learning, formulate criteria and protocols for automated electrical stimulation after the training phase has been completed. It is important to test many different combinations of activities and stimulation levels so that the control unit 30 may formulate the most accurate protocols and criteria for neuromodulation by electrical stimulation. The more data points available to the control unit 30, the more effectively, accurately, and efficiently the machine learning will be performed.

The duration of the training phase will vary depending on the patient 12. For example, a patient 12 who frequently provides feedback will complete the training phase faster than a patient 12 who infrequently provides feedback or requires prompting prior to providing feedback. In exemplary embodiments, the training phase may take 4-6 weeks, though more or less time may be necessary. The number of tasks performed each day by the patient 12, as well as the number of times that electrical stimulation is applied to the patient 12 by the pulse generator 20, may vary depending on the embodiment and the patient 12. For example, the type of pulse generator 20, the lead 22 location, the patient's 12 condition, and other considerations may affect the number of tasks performed by the patient 12 during the training phase.

Figure 17:
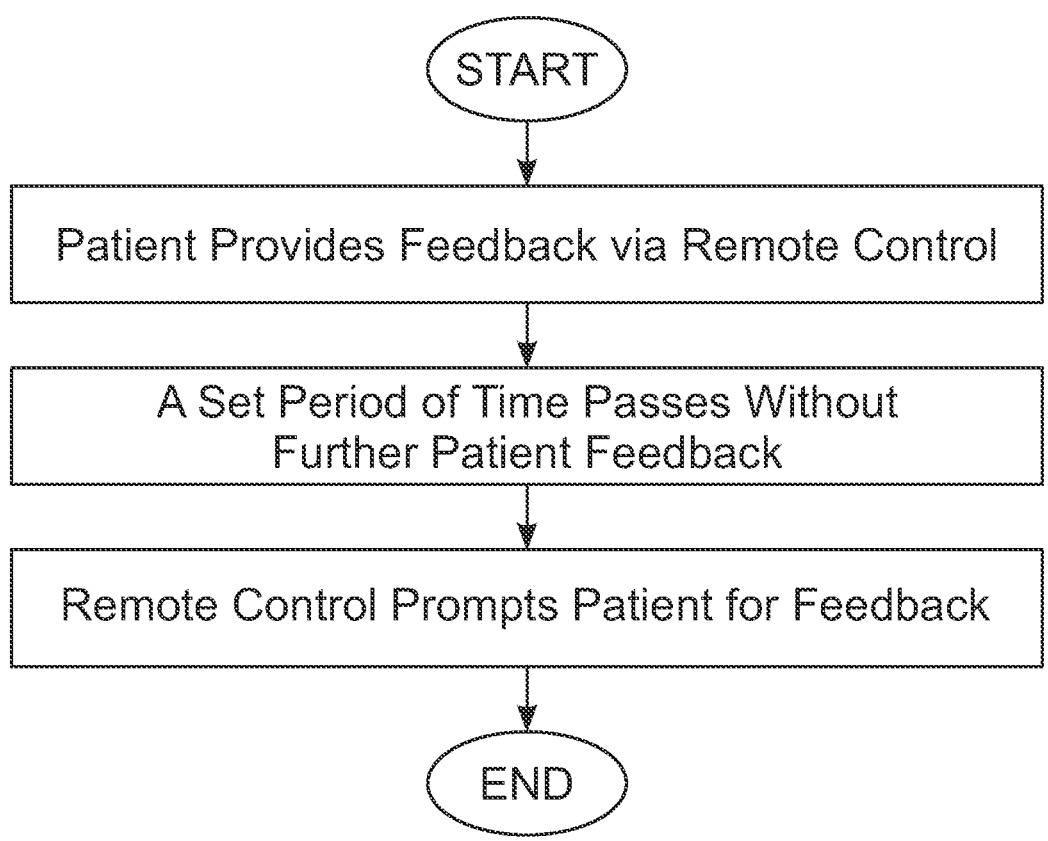
FIG. 17 is a flowchart illustrating prompting for patient feedback of a method and system for automated neuromodulation through machine learning in accordance with an example embodiment.

As shown in FIG. 17, the system 10 may be configured to ensure that the patient 12 provides consistent feedback at appropriate intervals. If too long has passed since the patient 12 has provided any feedback, the remote control 40 may prompt the patient 12 for feedback. The prompt may be provided by, for example, vibrating the remote control 40 or providing an audible or visible alarm. In any case, the remote control 40 may continue to prompt the patient 12 until feedback is provided. The period of time without feedback before which the remote control 40 will prompt for feedback may vary in different embodiments, and may be set by the control unit 30.

Figure 18:
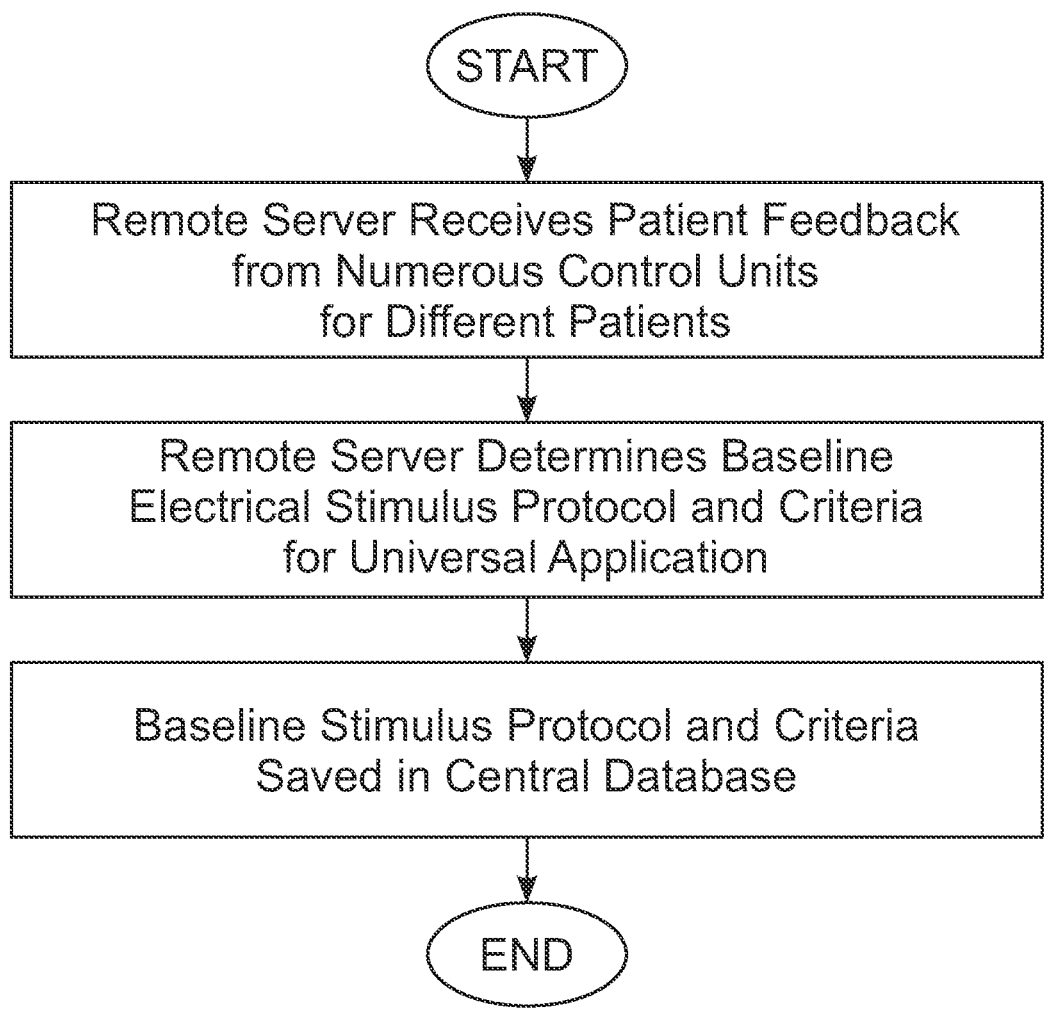
FIG. 18 is a flowchart illustrating the formulation of a baseline electrical stimulus protocol and criteria of a method and system for automated neuromodulation through machine learning in accordance with an example embodiment.

As shown in FIG. 18, a baseline stimulus protocol and criteria may be formulated through machine learning being applied to data from a large number of patients 12, each having a pulse generator 20 and accompanying remote control 40. A central database 52 may be maintained to store the data from all of the patients 12 in an anonymized format. The central database 52 may be stored on one system, or may be distributed across a network. In an exemplary embodiment, the central database 52 may be connected to a remote server 50 which processes and transfers the data to be stored on the central database 52.

As shown in FIG. 18, the remote server 50 may receive patient feedback from numerous control units for numerous patients 12. As discussed previously, the remote server 50 may receive a large amount of data related to each patient 12, including effective and ineffective levels of electrical stimulation for different tasks or activities. The data may include location, position, speed, orientation, or other data taken by the sensor 24 of each patient 12. The data may also include information such as the condition being treated, the implantation site of the pulse generator 20 and/or leads 22, the types of pulse generators 20 and leads 22 used, age, race, sex, and other information which is relevant to formulating the baseline protocol and criteria for neuromodulation.

Using the data collected from all of the patients 12, the remote server 50 may determine the baseline electrical stimulus protocol and criteria for universal application. This baseline stimulus protocol and criteria may be saved in the central database 52 for access by control units 30 of additional patients 12 whose data will similarly be transferred back to the central database 52 to improve the baseline protocol and criteria.

Figure 19:
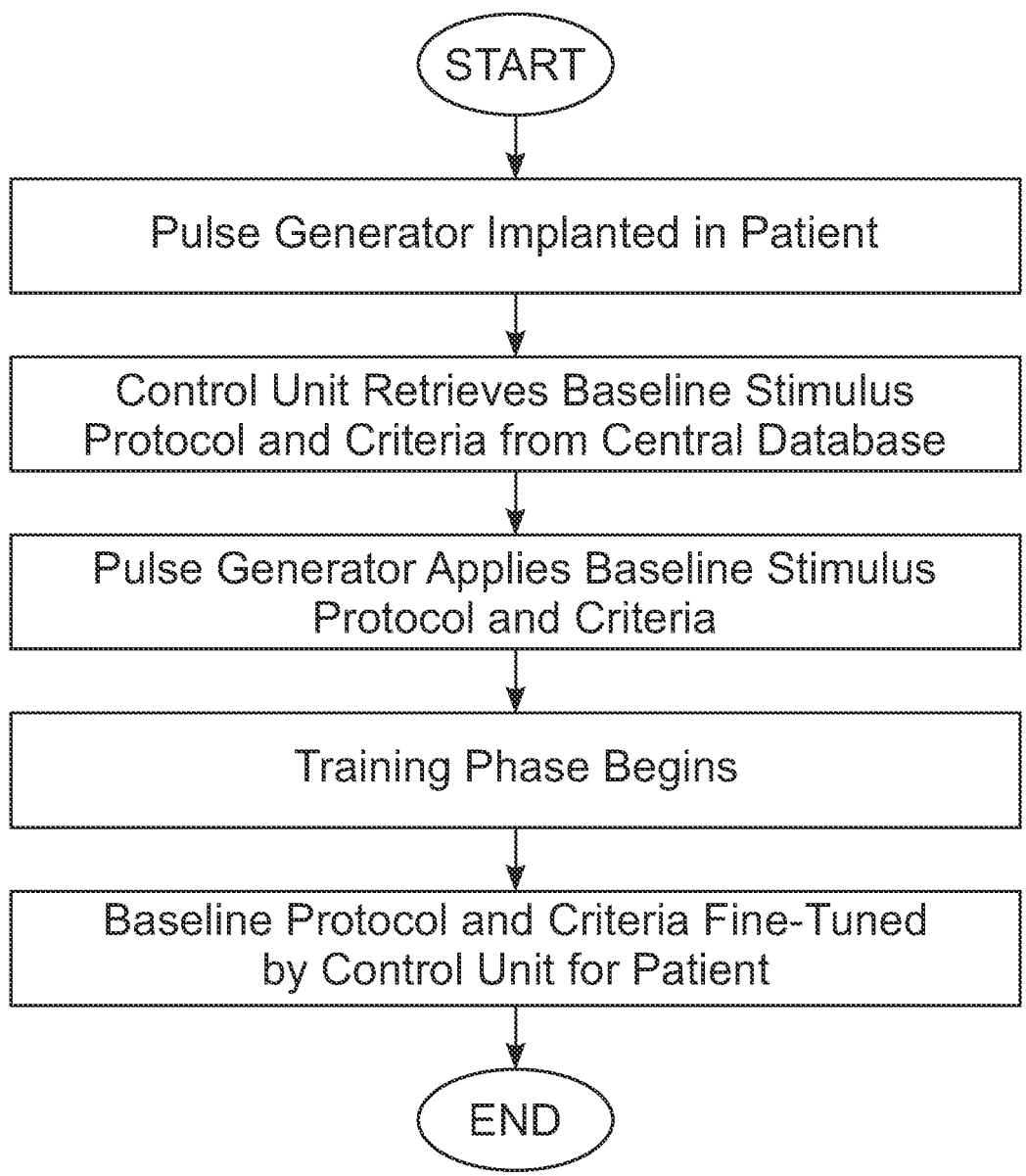
FIG. 19 is a flowchart illustrating fine-tuning of a neuromodulation protocol and criteria of a method and system for automated neuromodulation through machine learning in accordance with an example embodiment.

FIG. 19 illustrates an exemplary embodiment in which a baseline protocol and criteria are applied to a new patient 12 based on data collated and processed from previous patients 12. As shown, the pulse generator 20 and/or lead 22 is first implanted in the patient 12. The control unit 30 will communicate with the remote server 50 to provide various information and data related to the particular patient 12 being treated. For example, the control unit 30 may communicate the patient's 12 condition, mobility, age, sex, race, weight, height, body position, implantation site, pulse generator 20 type, lead 22 type, and the like.

The remote server 50 will use this data to retrieve from the control database 52 a neuromodulation criteria and protocol which has been shown to be favorable by past patient's 12 with similar information and data (such patients 12 with similar conditions, age, sex, race, height, etc.). The pulse generator 20 will then be configured to automatically apply the baseline criteria and protocol for some level of automation while the training phase commences. As the training phase continues, the baseline levels will be fine-tuned by the control unit 30 to be optimal for that particular patient 12. The baseline electrical stimulation protocols may be collated and desirable electrical stimulation protocols/programs may be stored in a central database 52, where machine learning and artificial intelligence is used to predict the most effective electrical stimulation protocol/program for a particular patient 12 based on feedback.

Figure 20:
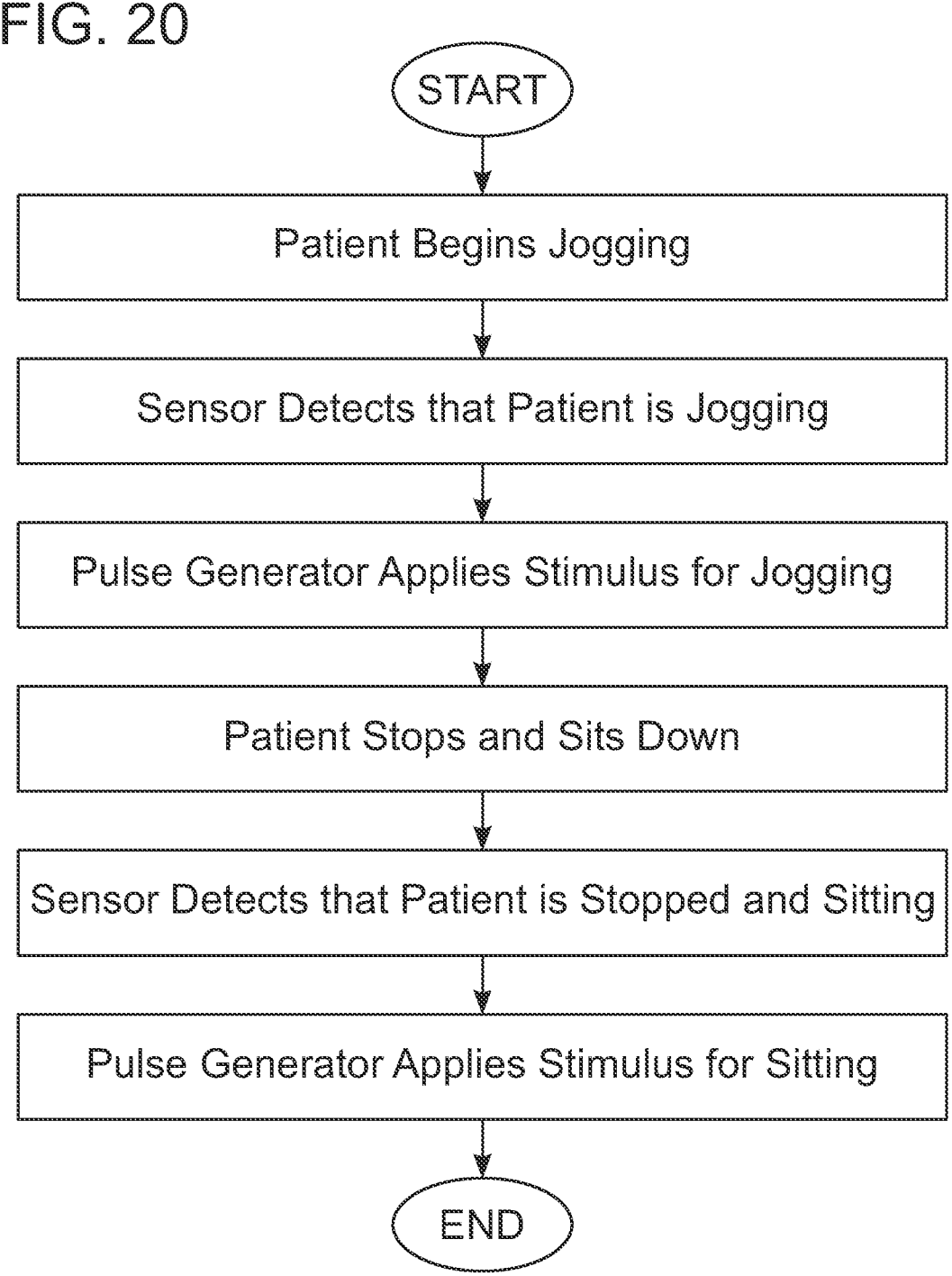
FIG. 20 is a flowchart illustrating operation of a method and system for automated neuromodulation through machine learning in accordance with an example embodiment.

FIG. 20 illustrates an exemplary method of automatically applying neuromodulation criteria and protocol to a patient 12 based on machine learning from the training phase. In the example, the patient 12 begins jogging. The sensor 24 detects that the patient 12 is jogging and applies a level and period of electrical stimulation which has previously been indicated by the patient 12 as favorable when jogging. When the patient 12 eventually stops and sits down, the sensor 24 will detect that the patient 12 is stopped and sitting, and apply appropriate electrical stimulation for sitting as learned from the training phase.

In some embodiments, the system 10 may utilize a mobile device 46 such as a smart phone or smart watch 47 to function as both a remote control 40 and a sensor 24. Modern mobile devices 46 typically include numerous sensors, including GPS, accelerometers, gyroscopes, physiological sensors such as heart rate sensors, and the like. This data can be extremely relevant to the machine learning, as more information related to a patient's activities at any certain time will result in more accurate criteria and protocol to be applied for neuromodulation of that patient 12.

For example, a mobile device 46 may provide the system 10 with the number of steps taken by the patient 12 per day, flights of stairs climbed, amount of sleep, amount of distance traveled, and the like. The pulse generator 20 may be communicatively connected to a smart phone of the patient so as to access various information from the smart phone, such as but not limited to a pedometer reading, screen time, sleep time, heart rate, blood pressure, blood sugar, and activity level. This data may be transmitted to the central database 52 for processing.

This information can all be utilized to help adjust programming to maximize patient function. The system 10 may also be integrated with location settings of a mobile device 46 such as a smart phone or smart watch 47. This information allows the system 10 to predict how well a patient can move, walk, or ambulate based on program settings. All of this data may be taken into account when formulating the fine-tuned criteria and protocol for that particular patient 12. For example, the system 10 may fine-tune the criteria and protocol to maximize the patient function, movement, sleep, and heart rate to find the ideal stimulation parameters and criteria for that particular patient 12.

Unless otherwise defined, all technical and scientific terms used herein have the same meaning as commonly understood by one of ordinary skill in the art to which this invention belongs. Although methods and materials similar to or equivalent to those described herein can be used in the practice or testing of the method and system for automated neuromodulation through machine learning, suitable methods and materials are described above. All publications, patent applications, patents, and other references mentioned herein are incorporated by reference in their entirety to the extent allowed by applicable law and regulations. The method and system for automated neuromodulation through machine learning may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

What is claimed is:

1. An automated neuromodulation system, comprising:
a plurality of leads, wherein each of the plurality of leads is implanted within one of a plurality of patients, wherein each of the plurality of leads is connected to or near an afflicted area of one of the plurality of patients;
a plurality of pulse generators, wherein each of the plurality of pulse generators is implanted within one of the plurality of patients and is in communication with one of the plurality of leads, wherein each of the plurality of leads applies an electrical stimulation to the afflicted area of one of the plurality of patients;
a plurality of control units, wherein each of the plurality of control units is in communication with one of the plurality of pulse generators;
a plurality of sensors, wherein each of the plurality of sensors is included in one of the plurality of pulse generators that is implanted within one of the plurality of patients, and wherein each of the plurality of sensors is in communication with one of the plurality of control units, wherein each of the plurality of sensors senses one or more of a position, an orientation, a movement, and a speed to produce sensor data of one of the plurality of patients;
a plurality of remote controls, wherein each of the plurality of remote controls is in communication with one of the plurality of control units and one of the plurality of pulse generators, wherein each of the plurality of remote controls provides only two possible user-inputs for providing a patient feedback to the electrical stimulation and for providing a patient feedback to a lack of the electrical stimulation, wherein a first user-input of the only two possible user-inputs comprises a positive patient feedback and wherein a second user-input of the only two possible user-input comprises a negative patient feedback; and a remote server including a central database, wherein each of the plurality of control units is communicatively connected to the remote server;

wherein each of the plurality of control units transmits the patient feedback and the sensor data received from the plurality of sensors of one of the plurality of patients at a time of the patient feedback to the remote server;

wherein the remote server processes historical patient feedback and sensor data of the plurality of patients that occurred during execution of a training phase stimulation protocol with the plurality of pulse generators and plurality of leads to formulate, in accordance with a machine learning algorithm, an optimal baseline electrical stimulation protocol that is applied to a new patient responsive to the sensor data of the new patient without requiring feedback from the new patient.

2. The automated neuromodulation system of claim 1, wherein the remote server is configured to continuously update the baseline electrical stimulation protocol based on the patient feedback and the sensor data at the time of the patient feedback received from the plurality of control units.

3. The automated neuromodulation system of claim 2, wherein each of the plurality of pulse generators is configured to automatically apply the baseline electrical stimulation protocol.

4. A method of developing an automated neuromodulation protocol for a new patient using the automated neuromodulation system of claim 1, comprising the steps of:
receiving the patient feedback from the plurality of control units by the remote server;
receiving the sensor data of each of the plurality of patients at the time of the patient feedback by the remote server;
processing the patient feedback and the sensor data of each of the plurality of patients at the time of the patient feedback to formulate an electrical stimulation protocol for a new patient.

5. The method of claim 4, further comprising the step of continuously updating the electrical stimulation protocol for the new patient by the remote server based on the patient feedback and the sensor data at the time of the patient feedback received from the plurality of control units.

6. A method of developing an automated neuromodulation protocol for a new patient using the automated neuromodulation system of claim 1, comprising the steps of:
conducting a training phase with one or more of the plurality of patients during which different levels of the electrical stimulation are applied to the one or more of the plurality of patients while an activity is performed;
receiving the patient feedback by the remote server from one or more of the plurality of control units the training phase;
processing the patient feedback during the training phase to formulate an electrical stimulation protocol for a new patient by the remote server.

7. The method of claim 6, further comprising the step of continuously updating the electrical stimulation protocol for the new patient by the remote server based on the patient feedback during the training phase.

8. The automated neuromodulation system of claim 1, wherein the remote server additionally processes sensor data to identify that at least one of the plurality of patients is currently performing an action that should be tested without the action having been previously programmed in the training phase stimulation protocol and wherein, based on the remote server having identified the action that should be tested, the remote server modifies the training phase stimulation protocol to test delivering stimulation during the action.

9. The automated neuromodulation system of claim 8, wherein, based on the remote server having modified the training phase stimulation protocol to test delivering stimulation during the action, the remote server further modifies the training phase stimulation protocol to prompt the at least one of the plurality of patients to perform the action.

10. An automated neuromodulation system, comprising:
a plurality of leads, wherein each of the plurality of leads is implanted within one of a plurality of patients, wherein each of the plurality of leads is connected to or near an afflicted area of one of the plurality of patients;
a plurality of pulse generators, wherein each of the plurality of pulse generators is implanted within one of the plurality of patients and is in communication with one of the plurality of leads, wherein each of the plurality of leads applies an electrical stimulation to the afflicted area of one of the plurality of patients;
a plurality of control units, wherein each of the plurality of control units is in communication with one of the plurality of pulse generators;
a plurality of sensors, wherein each of the plurality of sensors is included in one of the plurality of pulse generators that is implanted within one of the plurality of patients, and wherein each of the plurality of sensors is in communication with one of the plurality of control units, wherein each of the plurality of sensors senses one or more of a position, an orientation, a movement, and a speed to produce sensor data of one of the plurality of patients;
a plurality of remote controls, wherein each of the plurality of remote controls is in communication with one of the plurality of control units and one of the plurality of pulse generators, wherein each of the plurality of remote controls comprises at least one input for providing a patient feedback to the electrical stimulation; and
a remote server including a central database, wherein each of the plurality of control units is communicatively connected to the remote server;
wherein each of the plurality of control units transmits the patient feedback and the sensor data received from the plurality of sensors of one of the plurality of patients at a time of the patient feedback to the remote server;
wherein the remote server processes historical patient feedback and sensor data of the plurality of patients that occurred during execution of a training phase stimulation protocol with the plurality of pulse generators and plurality of leads to formulate, in accordance with a machine learning algorithm, an optimal baseline electrical stimulation protocol that is applied to a new patient responsive to the sensor data of the new patient without requiring feedback from the new patient.

\* \* \* \* \*